United States Patent
Johnson et al.

(10) Patent No.: US 10,940,218 B2
(45) Date of Patent: *Mar. 9, 2021

(54) TREATMENT OF MENINGIOMAS USING PHENYLBENZOTHIAZOLE, STILBENE, BIPHENYLALKYNE, OR PYRIDINE DERIVATIVES

(71) Applicant: MAYO FOUNDATION FOR MEDICAL EDUCATION AND RESEARCH, Rochester, MN (US)

(72) Inventors: Geoffrey B. Johnson, Rochester, MN (US); Val J. Lowe, Rochester, MN (US); Mark A. Nathan, Rochester, MN (US); Joseph E. Parisi, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 300 days.

This patent is subject to a terminal disclaimer.

(21) Appl. No.: 15/472,763

(22) Filed: Mar. 29, 2017

(65) Prior Publication Data

US 2017/0196999 A1    Jul. 13, 2017

Related U.S. Application Data

(62) Division of application No. 14/411,577, filed as application No. PCT/US2013/047878 on Jun. 26, 2013, now abandoned.

(60) Provisional application No. 61/665,000, filed on Jun. 27, 2012.

(51) Int. Cl.
| | |
|---|---|
| *A61K 51/00* | (2006.01) |
| *A61M 36/14* | (2006.01) |
| *A61K 51/04* | (2006.01) |
| *A61K 31/428* | (2006.01) |
| *A61K 49/00* | (2006.01) |
| *A61K 49/10* | (2006.01) |
| *A61K 45/06* | (2006.01) |

(52) U.S. Cl.
CPC ........ *A61K 51/0453* (2013.01); *A61K 31/428* (2013.01); *A61K 45/06* (2013.01); *A61K 49/00* (2013.01); *A61K 49/10* (2013.01)

(58) Field of Classification Search
CPC .... A61K 51/0453; A61K 45/06; A61K 49/00; A61K 49/10; A61K 31/428
USPC ...................................................... 424/1.89
See application file for complete search history.

(56) References Cited

U.S. PATENT DOCUMENTS

| | | | |
|---|---|---|---|
| 5,980,861 A | 11/1999 | Hnatowich et al. | |
| 6,001,331 A | 12/1999 | Caprathe et al. | |
| 6,096,874 A | 8/2000 | Wallace et al. | |
| 6,696,039 B2 | 2/2004 | Kung et al. | |
| 6,858,633 B1 | 2/2005 | Stevens et al. | |
| 7,270,800 B2 | 9/2007 | Klunk et al. | |
| 7,311,893 B2 | 12/2007 | Gervais et al. | |
| 9,259,495 B2 | 2/2016 | Johnson et al. | |
| 2003/0149250 A1 | 8/2003 | Kung et al. | |
| 2005/0080075 A1* | 4/2005 | Nichols | A61K 47/60 514/225.5 |
| 2007/0031328 A1 | 2/2007 | Kung | |
| 2008/0219931 A1* | 9/2008 | Klunk | A61K 49/0002 424/9.2 |
| 2008/0267981 A1* | 10/2008 | Janda | A61K 47/48561 424/181.1 |
| 2008/0305040 A1* | 12/2008 | Klunk | G01N 33/5088 424/1.65 |
| 2009/0257949 A1 | 10/2009 | Hefti et al. | |

FOREIGN PATENT DOCUMENTS

WO    2012/051170 A2    4/2012

OTHER PUBLICATIONS

Kumar et al. Cancer 1987, 57, 1274-1282.*
Mathis et al. J. Med. Chem. 2003, 46, 2740-2754.*
Foschini et al. Virchows Archiv. A Pathol. Anat. 1993, 422, 53-59.*
Rutten et al. J. Nucl. Med. Chem. 2007, 48, 720-725.*
Aho, et al., Immunohistochemical Visualization of Amyloid-β Protein Precursor and Amyloid-β in Extra- and Intracellular Compartments in the Human Brain, Journal of Alzheimer's Disease 20 (2010) 1015-28.
Astner, et al., Effect of 11C-Methionine-Positron Emission Tomography on Gross Tumor Volume Delineation in Stereotactic Radiotherapy of Skull Base Meningiomas, Int. J. Radiat. Oncol. Biol. Phys., vol. 72, No. 4, 2008, 1161-1167.
Bhojani, et al., Targeted Imaging and Therapy of Brain Cancer using Theranostic Nanoparticles, Mol. Pharm., Dec. 6, 2010 vol. 7(6), pp. 1921-1929.

(Continued)

*Primary Examiner* — Michael G. Hartley
*Assistant Examiner* — Sean R Donohue
(74) *Attorney, Agent, or Firm* — Quarles & Brady LLP

(57) ABSTRACT

A method and composition for treating a meningioma in a subject are disclosed. The method includes the step of administering to the subject a therapeutically effective amount of a composition including a cytotoxic agent associated with a phenylbenzothiazole derivative or a stilbene derivative or a biphenylalkyne derivative that accumulates within meningiomas. In one version of the method, the phenylbenzothiazole derivative is a compound of formula (V):

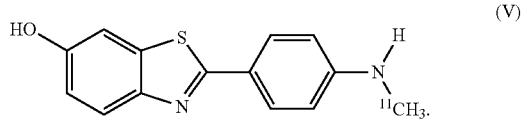

27 Claims, 7 Drawing Sheets

(56) References Cited

OTHER PUBLICATIONS

Chen, et al., A Novel Approach to a Bifunctional Photosensitizer for Tumor Imaging and Phototherapy, Bioconjugate Chem., vol. 16, 2005, pp. 1264-1274.

Foschini, et al., Amyloid stroma in meningiomas, Virchows Archive A Pathol. Anat., vol. 422, No. 1 (1993), 53-59.

Fu, et al., Ricin Toxin Contains Three Lectin Sites Which Contribute to its In Vivo Toxicity, Int. J. Innumopharmac., vol. 18, No. 12, pp. 685-692, 1996.

Ikonomovic, et al., Post-mortem correlates of in vivo PiB-PET amyloid imaging in a typical case of Alzheimer's disease, Brain : A Journal Of Neurology 2008;131:1630-45.

Kantarci, et al., Magnetic resonance spectroscopy, {beta}-amyloid load, and cognition in a population-based sample of cognitively normal older adults, Neurology 2011;77:951-8.

Koivunen, et al., PETamyloid ligand [11C]PIB uptake shows predominantly striatal increase in variant Alzheimer's disease, Brain (2008), 131, 1845-53.

Lasne, et al., Chemistry of β +-Emitting Compounds Based on Fluorine-18, Top. Curr. Chem. 2002, 201-258.

Lee, et al., Amyloid Deposits in Supratentorial Meningiomas—Clinicopathological and Immunohistochemical Study—Journal Abstract, vol. 24, No. 7 (Jul. 1995), 794-799.

Levine, Y10W b(1-40) fluorescence reflects epitope exposure in conformers of Alzheimer's β-peptide, Archives of Biochemistry and Biophysics 417 (2003) 112-122.

Lowe, et al., Comparison of 18F-FDG and PiB PET in cognitive impairment, Journal Of Nuclear Medicine : official publication, Society of Nuclear Medicine 2009;50:878-86.

Mathis, et al., Synthesis and Evaluation of 11C-Labeled 6-Subslituted 2-Arylbenzothiazoles as Amyloid Imaging Agents, Journal of Medicinal Chemistry, 2003, 46(13):2740-2754.

Matsunaga, et al., A pH-dependent conformational transition of Ab peptide and physicochemical properties of the conformers in the glial cell, Biochem. J. (2002) 361, 547-556.

Modha, et al., Diagnosis and Treatment of Atypical and Anaplastic Meningiomas: A Review, Neurosurgery, 2005, 57:538-550.

PCT International Search Report and Written Opinion, PCT/US13/147878, dated Feb. 10, 2014, 17 pages.

Roberts, et al., The Mayo Clinic Study of Aging: design and sampling, participation, baseline measures and sample characteristics, Neuroepidemiology 2008;30:58-69.

Rutten, et al., PET/CT of Skull Base Meningiomas Using 2-18F-Fluoro-L-Tyrosine:Initial Report, J Nucl Med 2007, 720-725.

Toh, et al., Differentiation Between Classic and Atypical Meningiomas With Use Of Diffusion Tensor Imaging, AJNR Am. J. Neuroradiol., 2008, 29:1630-1635.

Vision Biosystems Novocastra, Data Sheet—Beta Amyloid—mouse monoclonal antibody—NCL-B-Amyloid.

Wang, et al., Synthesis of carbon-11 labeled fluorinated 2-arylbenzothiazoles as novel potential PET cancer imaging agents, Biorg. Med. Chem. 2006, 14, 8599-607.

Yang, et al., Expression of PDGF and its receptor as well as their relationship to proliferating activity and apoptosis of meningiomas in human meningiomas, J. Clin. Neurosci. 2000, 8, (Supplement 1) 48-53.

\* cited by examiner

TREATMENT OF MENINGIOMAS USING PHENYLBENZOTHIAZOLE, STILBENE, BIPHENYLALKYNE, OR PYRIDINE DERIVATIVES

CROSS-REFERENCES TO RELATED APPLICATIONS

This application is a divisional application of U.S. patent application Ser. No. 14/411,577 filed Dec. 29, 2014, which is a 371 application of PCT/US2013/047878 filed Jun. 26, 2013, which claims priority from U.S. Patent Application No. 61/665,000 filed Jun. 27, 2012.

STATEMENT REGARDING FEDERALLY SPONSORED RESEARCH

Not Applicable.

BACKGROUND OF THE INVENTION

1. Field of the Invention

The invention relates to the treatment of meningiomas using a composition including a cytotoxic agent and a compound selected from phenylbenzothiazole derivatives, stilbene derivatives, biphenylalkyne derivatives, and imidazo[1,2-a]pyridine derivatives.

2. Description of the Related Art

Meningiomas are the second most common tumor inside the skull with an incidence of approximately six per 100,000, and meningiomas account for 13-26 percent of all primary intracranial tumors. Approximately 90% of meningiomas are benign, with the rest being more aggressive, or even malignant. The benign classifications include meningothelial meningioma, fibrous/fibroblastic meningioma, transitional (mixed) meningioma, psarnrnomatous meningioma, angiomatous meningioma, microcystic meningioma, secretory meningioma, lymphoplasmacyte-rich meningioma and metaplastic meningioma. The more aggressive classifications of meningiomas include, atypical meningioma, clear cell meningioma, chordoid meningioma, rhabdoid meningioma, papillary meningioma and anaplastic (malignant) meningioma.

Most often standard imaging leads to a confident diagnosis of benign meningioma. However, the variability of types of meningiomas corresponds with the wide range of possible appearances on standard imaging. In addition, many other types of tumors can arise in the membranes overlying the brain where meningiomas most commonly arise; pia, arachnoid and dura matter. These two factors can lead to a lack of diagnostic confidence with conventional diagnostic imaging. This lack of confidence can have dramatic and negative effects on a patient's medical care.

The majority of meningiomas can be confidently diagnosed based on conventional imaging, such as computed tomography (CT) and magnetic resonance imaging (MRI). When a mass in the dura is identified in a patient based on CT or MRI, the most likely diagnosis is meningioma. A minority of meningiomas contain calcifications, and most meningiomas have higher density than the surrounding brain. These findings are best evaluated by CT, and both increase confidence in the diagnosis of meningioma. Diagnostic confidence is also increased when a dural based mass has a "dural tail sign", or when it uniformly enhances with intravenous gadolinium. These findings are best evaluated on MRI. Stability or very slow growth of the mass over many months to years also increases confidence in the diagnosis of meningioma. With these criteria the majority of meningiomas located in the dura can be diagnosed with confidence, either at their initial identification on CT and MRI, or in time when they prove to be stable in size.

Beyond CT and MRI there are other adjunct methods currently used to help diagnose meningiomas. Angiography has historically been used to suggest the diagnosis of meningioma. Demonstration of arterial supply from meningeal vessels and delayed vascular blush on angiography are characteristic of meningiomas. However, these findings are neither sensitive nor specific, therefore CT and MRI have proven more useful than angiography for the diagnosis of meningiomas. Angiography is currently reserved for embolization of meningiomas as a primary therapy, or to reduce the risk of intraoperative hemorrhage. Surgery results in diagnosis/treatment of meningiomas, but reported surgical mortality rate is as high as 14.3%. Lumbar puncture with cerebrospinal fluid (CSF) testing is not useful for diagnosing meningiomas. However, CSF testing is potentially helpful for diagnosing metastatic disease. Leptomeningeal invasion can give rise to tumor cell dissemination in the CSF, which can be detected by lumbar puncture with cytology, however this is often falsely negative. There are no good laboratory tests available for the diagnosis of meningioma. Meningiomas are most often diagnosed incidentally with imaging. Physical exam and clinical history are often normal in patients with meningiomas. When there are signs and symptoms related to a meningioma, they are most often non-specific, related to the mass effect of the meningioma.

Thus, there are problems with the current methods for diagnosing meningiomas. A minority of meningiomas can not be diagnosed with confidence based current imaging methods. Meningiomas can look like other tumors. Meningiomas can occur in locations where other tumors are common. Meningiomas can occur elsewhere in the body outside of the dura. Although meningiomas are more common, many less common tumors can mimic the appearance of a meningioma. Therefore, the diagnosis of meningioma can not always be made with confidence based on CT and MRI alone, and sometimes when the diagnosis of meningioma is felt to be confident, it is incorrect. This is particularly important in cases where the different diagnoses being considered require very different therapy, or the real diagnosis is not even considered, such as with metastatic malignancy.

In patients with meningiomas that have an atypical imaging appearance, the differential diagnosis based on CT and MRI is often broader, less confident and includes metastatic disease. Meningiomas can have widely varied appearances on CT and MRI, such as cystic changes, adjacent reactive bony proliferation, and adjacent reactive brain parenchyma edema. Examples of meningiomas mistaken for other tumors are plentiful. Misdiagnoses include: orbital metastatic carcinoma; carcinoid tumor; intramedullary spinal tumor; calvarial metastasis; schwannoma; idiopathic hypertrophic pachymeningitis, pituitary adenoma and glial or metastatic tumors.

In some patients, tumors are identified within the dura in locations where other known common tumors can occur. For example, in the cerebropontine angle, the differential diagnosis for a tumor commonly includes schwannoma and meningioma, and less likely metastasis, melanoma, sarcoidosis, tuberculosis, Erdheim-Chester, lymphoma, paraganglioma, chordoma. In the region of the sella turcica, the differential diagnosis for a tumor commonly includes pituitary adenoma and meningioma, and less likely craniopharyngioma, glioma, germinoma, hamartoma, aneurysm, trigeminal schwannoma, pituitary carcinoma, chordoma, metastasis and infection. Meningiomas can occasionally occur outside of the cranial vault and outside of the dura, making their correct diagnosis in these locations much more difficult. When tumors associated with the dura are found in the spine, the differential commonly includes meningioma, schwannoma, neurofibroma and metastasis. Meningiomas can occur outside the dura in the cervical spine. Other less common extradural locations where meningiomas have been found include the mediastinum, the ventricle of the brain, lungs, mandible and bone. Rarely meningiomas can even metastasize from the dura to distant locations, such as to the lungs.

Numerous articles have demonstrated that although most dural tumors can be confidently diagnosed as meningiomas based on CT and MRI, uncommonly many other tumors can mimic the appearance of a meningioma. Therefore, the differential for dural based masses that look like meningiomas on CT and MRI is very broad. The general categories for etiologies of these meningioma-like dural masses include metastatic disease, lymphoma, multiple myeloma/plasmacytoma, primary dural tumors, infections, inflammatory tumors, and other systemic diseases.

The differentiation between meningioma and dural metastasis in particular can be very difficult based on current imaging methods. This differentiation is critical, as often dural metastasis require far more aggressive medical and surgical management than meningiomas. Since meningiomas are common, even in patients with a known metastatic malignancy, the possibility remains that a dural based mass represents a coincidental meningioma. Dural metastases are found at autopsy in 8-9% of patients with advanced systemic cancer. Prostate, breast, lung and stomach cancer are the most common malignancies metastasizing to the dura. However, renal, bladder, thyroid, colon, rectal, pancreatic, gallbladder, hepatobiliary, cervical, endometrial, choriocarcinoma, mesothelioma, neuroblastoma, sarcoma, seminoma, and other adenocarcinomas have also been reported to metastasize to the dura. The diagnosis can be further confused since, the patient's primary malignancy may be unknown and/or the dural metastasis may be the initial presentation of systemic malignancy. Furthermore, metastasis to the dura can occur long after the patient has been in complete remission.

There have been advances in imaging for the diagnosis of meningioma. Imaging modalities continue to advance and new techniques in MRI and molecular imaging, may prove helpful with the differentiation between meningioma and other tumors such as metastasis. The most promising modalities are Dynamic contrast MRI with cerebral blood volume mapping and octreotide-analogue based positron emission tomography/computed tomography (PET/CT). Diffusion tensor MRI may help to tell benign from aggressive meningiomas, based on one small preliminary study. However, diffusion tensor MRI has not been shown to differentiate meningiomas form other types of tumors, such as metastasis.

Dynamic contrast MRI with cerebral blood volume mapping has shown some promise in helping to differentiate meningiomas from metastasis in at least two small studies. With this technique intravenous contrast enhanced MRI is used to generate cerebral blood volume maps of the brain and surrounding tissues. These maps are used to measure the relative cerebral blood volume of the tumor compared to brain tissue as an internal control. These small preliminary studies suggest that the relative cerebral blood volume of meningiomas tends to be higher then the relative cerebral blood volume of metastatic tumors. This method is unproven, but shows promise for differentiating meningiomas from metastasis. It is as yet unclear if dynamic contrast MRI techniques will be helpful for differentiating meningiomas from other types of tumors. In addition, intravenous MRI contrast agents are required to perform these studies, therefore patients with renal failure are not able to undergo these exams. This is because, patients with renal failure are at risk to develop nephrogenic systemic fibrosis if they receive gadolinium containing intravenous MRI contrast agents. Nephrogenic systemic fibrosis is a serious condition involving fibrosis of skin, joints, eyes, and internal organs, that has been linked to the use of at least 4 of the 5 intravenous MRI contrast agents currently approved by the U.S. Food and Drug Administration; Omniscan, Multihance, Magnevist, and OptiMARK.

Fluorodeoxyglucose (FDG)-PET or FDG-PET/CT can be used in the imaging of dural tumors. The standard uptake value (SUV) of FDG seen within a meningioma has been shown to be somewhat predictive of how aggressive a meningioma is, and how likely the meningioma will be to recur if surgically removed. Meningiomas that do take up significant FDG are usually atypical or even malignant. However, since meningiomas and the other tumors that are seen in the same locations can have variable FDG uptake on FDG-PET/CT, there is limited use of FDG-PET/CT for the diagnosis of meningioma. For example, often the differential for a tumor based on CT and MRI includes meningioma versus other tumors, such as a schwannoma, that both have little or no FDG uptake. Thus FDG-PET/CT is only of limited help in the diagnosis of meningioma in these situations. For other tumors, the differential based on CT and MRI includes aggressive meningioma versus other tumors, such as metastasis, that both have moderate to high FDG uptake. Again, in this situation FDG-PET/CT is of limited value. When the differential includes benign meningioma versus metastasis, FDG-PET/CT can be helpful. In this case, if the tumor in question has low or no FDG uptake, then the diagnosis of metastasis is less likely and meningioma more likely. However, even in this situation other tumors that do not take up FDG remain on the differential. Perhaps due to the above reasons, there are no studies to date that show FDG-PET/CT can help differentiate meningiomas from dural metastasis.

FDG is the only PET tracer currently approved by the U.S. Food and Drug Administration for tumor imaging. However, many experimental PET tracers are available. PET/CT performed with some of these experimental tracers may prove helpful in the diagnosis of meningiomas, but most are nonspecific. C11-methionine is taken up by some meningiomas. C11-methionine is taken-up in a nonspecific manner, thought to be due in large part to cellular protein production. Therefore C11-methionine is increased in many actively growing tumors. C11-methionine, similar to FDG, would likely not be taken-up by the majority of meningiomas, which are not fast growing. C11-methionine would not likely be useful for differentiating between aggressive meningiomas and dural metastasis, since both would likely have an increased SUV. 2-F-18-fluoro-L-tyrosine is taken up by some meningiomas. 2-F-18-fluoro-L-tyrosine is taken up in a non-specific manner by cells undergoing DNA synthesis, such as cells that are multiplying. Therefore, 2-F-18-fluoro-L-tyrosine has similar benefits and limitations to C11-methionine with regard to imaging of meningiomas. 16 alpha[F-18]fluoro-17 beta-oestradiol (F 18-FES) binds to estrogen receptors and is taken up by some, but not all meningiomas in one small preliminary study. Therefore, F18-FES-PET/CT may not prove to be highly sensitive for meningiomas. In addition, F18-FES binds to other tumors that express estrogen receptors, such as endometrial cancer, potentially making F18-FES nonspecific for meningiomas.

Radioactive tracers that emit single photons are used in planar nuclear imaging and single photon emission computed tomography (SPECT), and can be used in imaging of meningiomas. Many single photon tracers are approved for medical imaging use by the U.S. Food and Drug Administration. However, like most PET tracers, most single photon emitting tracers are nonspecific for meningiomas. For example, Thallium-201 SPECT imaging is somewhat useful for predicting histological types of meningiomas, but is nonspecific and is not useful for diagnosing meningiomas.

Meningiomas have been shown to express somatostatin 2 receptors and can therefore be imaged by octreotide (brand name Sandostatin, Novartis Pharmaceuticals, CAS #83 150-76-9, ATC code HO1CB02) and other somatostatin analogues. Octreotide is most commonly used for imaging of neuroendocrine tumors and can be used in SPECT or PET imaging. Octreotide can be linked to (111)Indium, which is a single photon emitter used in planar and SPECT imaging, or can be linked to 68Gallium, which is a positron emitter used in PET or PET/CT imaging. (111)indium-octreotide is a well studied tracer that binds somatostatin receptors, and is taken up by meningiomas. (111)Indium-Octreotide is approved for imaging by the U.S. Food and Drug Administration, whereas 68Ga-DOTATOC and 68Ga-DOTANOC are currently experimental labeled octreotide analogues. 1,4,7,10-tetraazacyclododecane-N,N',N'',N'''-tetraaceticacid (DOTA) is used to link 68Ga to one of at least 2 octreotide analogues, 1-Nal3-octreotide (NOC) or D Phe1-Tyr3-octreotide (TOC), thus they are called 68Ga-DOTANOC or 68Ga-DOTATOC. More is currently published on 68Ga-DOTATOC. In one study, 68Ga-DOTANOC-PET/CT may result in less radiation to patients than 68Ga-DOTATOC-PET/CT.

Octreotide appears to have good sensitivity for meningiomas, but is not perfect. Despite close to 100% of meningiomas reported to express somatostatin receptors, specifically receptor 2, sensitivity by imaging is lower. Some of the false negative studies may be due to small volume of some tumors. However, another theory is that an intact blood brain barrier may prevent octreotide from labeling some meningiomas. SPECT imaging, even when combined with CT, lacks the resolution of PET imaging and is generally considered inferior as a modality. (68)Gallium-DOTATOC-PET/CT shows better resolution. (68)Gallium-DOTATOC-PET/CT also shows a high signal to background ratio in meningiomas, since the normal brain does not take up octreotide. Octreotide tracers shows strongest uptake in neuroendocrine tumors, neuroectodermal tumors, renal cell carcinoma, small cell lung cancer, breast cancer, prostate cancer and malignant lymphoma. In addition to meningioma, (68)Gallium-DOTATOC is taken up by other tumors that may be on the differential for a dural mass, like some forms of metastatic disease, lymphoma, pituitary adenomas, and glial tumors. Octreotide imaging studies may have uses related to meningiomas beyond initial diagnosis. Octreotide imaging may prove helpful in follow-up post surgery for recurrent/residual meningioma, as MRI can be confusing due to postoperative changes. (68)Gallium-DOTATOC-PET/CT has been proposed as a good modality for the planning of focused forms of radiation therapy, such as fractionated stereotactic radiotherapy, and may see tumor extensions into the dense skull base better than other modalities.

Octreotide studies are time consuming to perform. (111) Indium-octreotide planar and SPECT imaging is routinely done at 24 hours, but 4 hours may be sufficient, detecting most meningiomas greater that 5 ml in volume. However, even 4 hours is a long wait when compared to the more conventional MRI and CT imaging, and is disruptive to patient's schedules. With (68)Gallium-DOTATOC-PET/CT, the scan is routinely performed 120 minutes after injection, with peak/plateau activity occurring somewhere between 60 and 120 minutes.

Thus, patients who have a history of cancer and find a new tumor in the meningeal membranes that envelope the brain are faced with a common diagnostic dilemma. Meningiomas are the most common benign intracranial tumors, detected on MRI in 0.9% of normal adults over the age of 45. Approximately 4% of individuals diagnosed with meningiomas have a history of cancer. In addition, the incidence of meningeal metastases in patients with late stage cancer is 9-10%. Approximately 1 out of 5 patients with meningeal metastases have limited or otherwise controlled cancer at the time of diagnosis. Therefore if the meningeal tumor represents a metastasis it could greatly alter the cancer stage, prognosis and plan of care.

CT and MRI are clearly inadequate for confident distinction of meningioma from meningeal metastasis in a single imaging evaluation. The diagnosis of meningioma is suggested when a tumor is detected in the meningeal membranes that envelope the central nervous system. Typical meningiomas enhance uniformly and have an enhancing dural tail (dural tail sign) extending along the meninges. However, meningiomas have a wide variety of appearances, and only 60% have this typical appearance. The dural tail sign can be seen with many other tumors, including metastases. In fact, approximately 44% of dural metastases have a dural tail according to a recent study from Memorial Sloan-Kettering Cancer Center, and can exactly mimic typical meningiomas on imaging. The insufficient specificity of MRI is exemplified in a blinded review of imaging from patients who had surgical resection of meningeal tumors at the Cleveland Clinic. In this selected population, the diagnosis of meningioma on MRI was only 50% specific and metastatic cancer was the most common mimic. Malignancy can be excluded with multiple follow-up MRI or CT scans over 1 to 2 years if they show stability, or very slow growth. Surgical biopsy is the only quick and reliable option available to definitively differentiate meningiomas from other tumors.

Therapy for meningiomas and metastases differs greatly, and therefore improvements in diagnosis would result in clinical benefit. Greater than 97% of meningiomas are World Health Organization grade I or II, and are considered nonmalignant. When a history of cancer is not clouding the diagnosis, most meningiomas can be monitored clinically and with imaging. A small subset of meningiomas cause symptoms due to mass effect, and therefore surgery or radiation may be required. Chemotherapy is not currently useful for treating meningiomas. These treatments are in stark contrast to the more aggressive, multimodality and systemic therapies that benefit patients with meningeal metastases. Unfortunately, because of inadequate diagnostic confidence with current imaging, many patients with probable meningiomas are compelled to have surgery primarily to confirm the diagnosis and only secondarily for the purpose of treating the tumor. Surgical mortality rates are as high as 7% and significant and permanent morbidity rates are as high as 40%, depending on location of the tumor.

Not only is there a need for alternative methods for diagnosing a meningioma in a patient, there is currently no effective pharmacological therapy to treat meningiomas either alone or as a neoadjuvant or adjuvant in conjunction with radiation and/or surgery. Surgery and/or radiation can be effective therapies for meningiomas in some patients, but both have risk of complications, morbidity and mortality. Meningiomas that are too large, in difficult locations, or involving critical sensitive structures cannot be effectively treated with radiation and/or surgery and are often left untreated despite progressive morbidity and ultimate mortality. Recurrent meningiomas that have been surgically resected or radiated have higher risk of complications if these therapies are repeated.

Meningiomas are the most common tumors inside the skull. They are seen in 0.9% of adults over the age of 45 according to a large Rotterdam study (N=2000), and that increases with age. In our review of the Mayo Clinic Study of Aging (N-834), meningiomas were seen in 2.5% of adults with an average age of 78. Given 300 million people in the US, based on 2010 census data, and 40% over the age of 45, and the 0.9% prevalence in the Rotterdam study, there are roughly 11 million US citizens with meningiomas detectable on MRI. A small but significant percentage of these may benefit from targeted drug therapy. In our study, two patients had surgery and two had radiation, while many others have had multiple imaging studies as follow up. Thus, of 24 meningiomas, and one additional meningioma removed surgically prior to the study, 16% received therapy. So extrapolating from our data, roughly 2 million Americans currently over the age of 45 could benefit from therapy. Of note, one of the resected tumors recurred. As expected, none of the tumors in our population were treated with drug therapy, as there is no effective drug therapy.

Therefore, it can be appreciated that there is a need for methods and compositions for the treatment of meningiomas.

SUMMARY OF THE INVENTION

The present invention addresses the foregoing needs by providing a method and composition for treating a meningioma in a subject. The method includes the step of administering to the subject a therapeutically effective amount of a composition including a cytotoxic agent associated with a phenylbenzothiazole derivative or a stilbene derivative or a biphenylalkyne derivative or an imidazo[1,2-a]pyridine derivative that accumulates within meningiomas.

Meningiomas are the most common tumors found inside the skull. Meningiomas are mostly benign, but can cause severe mortality and even death mostly due to mass effect. We have discovered that the compound of formula (V) below, Pittsburgh compound B (PiB), a phenylbenzothiazole derivative,

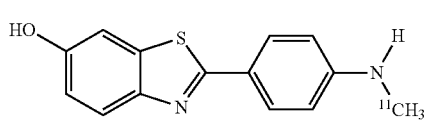
(V)

accumulates in meningiomas and may bind to a novel specific target within meningiomas. Our invention is the use of this new technology to deliver a therapeutic agent via the blood stream to a meningioma and therefore slow or halt its growth or reduce the size of the tumor. The goal is halt or reverse the progression of symptoms due to mass effect, and prevention of recurrence of meningioma after radiation and/or surgery. This new drug therapy could avoid the risks of current therapy, increase the success of current therapy and/or deliver therapy to patients who cannot be treated with current therapy.

In one aspect, the invention provides a method for treating a meningioma in a subject. The method includes the step of administering to the subject a therapeutically effective amount of a composition including a cytotoxic agent associated with a compound of formula (I):

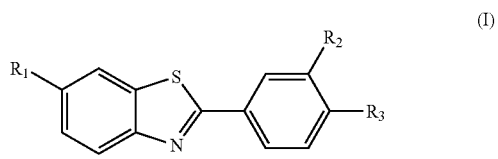
(I)

The compound is targeted to any meningiomas in the subject. $R_1$, $R_2$ and $R_3$ in Formula (I) can be independently selected from H, OH, halogen, substituted or unsubstituted alkyl, substituted or unsubstituted alkoxy, substituted or unsubstituted amino, and substituted or unsubstituted carboxylate. In one version of the method, before the step of administering to the subject the therapeutically effective amount of the composition, one administers to the subject a detectable amount of the compound of formula (I) wherein at least one of the atoms in $R_1$ or $R_2$ or $R_3$ is replaced with $^3$H, $^{11}$C, $^{13}$C, $^{14}$C, $^{13}$N, $^{15}$O, $^{75}$Br, $^{76}$Br, $^{18}$F, $^{19}$F, $^{68}$Ga, $^{82}$Rb, $^{111}$In, $^{123}$I, $^{125}$I, $^{131}$I, $^{201}$Tl, and $^{99m}$Tc, and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In another aspect, the invention provides a method for treating a meningioma in a subject. The method includes the step of administering to the subject a therapeutically effective amount of a composition including a cytotoxic agent associated with a compound of formula (II):

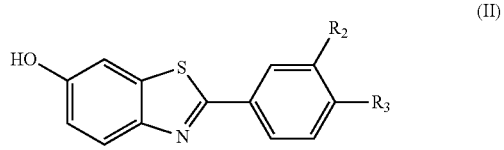
(II)

The compound is targeted to any meningiomas in the subject. $R_2$ and $R_3$ in Formula (II) can be independently selected from H, OH, halogen, substituted or unsubstituted alkyl, substituted or unsubstituted alkoxy, substituted or unsubstituted amino, and substituted or unsubstituted carboxylate. In one version of the method, before the step of administering to the subject the therapeutically effective amount of the composition, one administers to the subject a detectable amount of the compound of formula (II) wherein at least one of the atoms in $R_2$ or $R_3$ is replaced with $^3H$, $^{11}C$, $^{13}C$, $^{14}C$, $^{13}N$, $^{15}O$, $^{75}Br$, $^{76}Br$, $^{18}F$, $^{19}F$, $^{68}Ga$, $^{82}Rb$, $^{111}In$, $^{123}I$, $^{125}I$, $^{131}I$, $^{201}Tl$, and $^{99m}Tc$, and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In yet another aspect, the invention provides a method for treating a meningioma in a subject. The method includes the step of administering to the subject a therapeutically effective amount of a composition including a cytotoxic agent associated with a compound of formula (III):

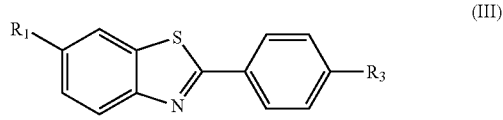

The compound is targeted to any meningiomas in the subject. $R_1$ and $R_3$ in Formula (III) can be independently selected from H, OH, halogen, substituted or unsubstituted alkyl, substituted or unsubstituted alkoxy, substituted or unsubstituted amino, and substituted or unsubstituted carboxylate. In one version of the method, before the step of administering to the subject the therapeutically effective amount of the composition, one administers to the subject a detectable amount of the compound of formula (III) wherein at least one of the atoms in $R_1$ or $R_3$ is replaced with $^3H$, $^{11}C$, $^{13}C$, $^{14}C$, $^{13}N$, $^{15}O$, $^{75}Br$, $^{76}Br$, $^{18}F$, $^{19}F$, $^{68}Ga$, $^{82}Rb$, $^{111}In$, $^{123}I$, $^{125}I$, $^{131}I$, $^{201}Tl$, and $^{99m}Tc$, and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In still another aspect, the invention provides a method for treating a meningioma in a subject. The method includes the step of administering to the subject a therapeutically effective amount of a composition including a cytotoxic agent associated with a compound of formula (IV):

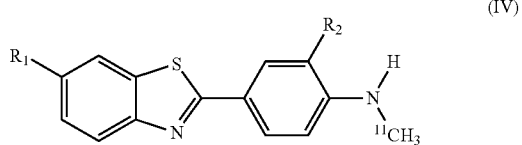

The compound is targeted to any meningiomas in the subject. $R_1$ and $R_2$ in Formula (IV) can be independently selected from H, OH, halogen, substituted or unsubstituted alkyl, substituted or unsubstituted alkoxy, substituted or unsubstituted amino, and substituted or unsubstituted carboxylate. In one version of the method, before the step of administering to the subject the therapeutically effective amount of the composition, one administers to the subject a detectable amount of the compound of formula (IV) wherein at least one of the atoms in $R_1$ or $R_2$ is replaced with $^3H$, $^{11}C$, $^{13}C$, $^{14}C$, $^{13}N$, $^{15}O$, $^{75}Br$, $^{76}Br$, $^{18}F$, $^{19}F$, $^{68}Ga$, $^{82}Rb$, $^{111}In$, $^{123}I$, $^{125}I$, $^{131}I$, $^{201}Tl$, and $^{99m}Tc$, and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In yet another aspect, the invention provides a method for treating a meningioma in a subject. The method includes the step of administering to the subject a therapeutically effective amount of a composition including a cytotoxic agent associated with a compound of formula (V):

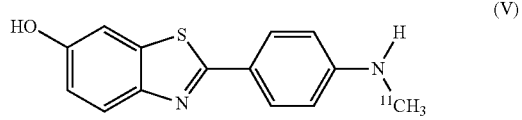

The compound is targeted to any meningiomas in the subject. In one version of the method, before the step of administering to the subject the therapeutically effective amount of the composition, one administers to the subject a detectable amount of the compound of formula (V), and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In still another aspect, the invention provides a method for treating a meningioma in a subject. The method includes the step of administering to the subject a therapeutically effective amount of a composition including a cytotoxic agent associated with a compound of formula (VI):

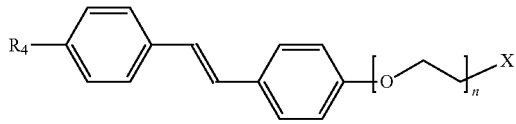

(VI)

$R_4$ and X in Formula (VI) can be independently selected can be selected from H, OH, halogen, substituted or unsubstituted alkyl, substituted or unsubstituted alkoxy, substituted or unsubstituted amino, and substituted or unsubstituted carboxylate; and n can be an integer from 0 to 10. The compound is targeted to any meningiomas in the subject. In one version of the method, before the step of administering to the subject the therapeutically effective amount of the composition, one administers to the subject a detectable amount of the compound of formula (VI) wherein X is replaced with an atom selected from the group consisting of $^{3}H$, $^{11}C$, $^{13}C$, $^{14}C$, $^{13}N$, $^{15}O$, $^{75}Br$, $^{76}Br$, $^{18}F$, $^{19}F$, $^{68}Ga$, $^{82}Rb$, $^{111}In$, $^{123}I$, $^{125}I$, $^{131}I$, $^{201}Tl$, and $^{99m}Tc$, and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In yet another aspect, the invention provides a method for treating a meningioma in a subject. The method includes the step of administering to the subject a therapeutically effective amount of a composition including a cytotoxic agent associated with a compound of formula (VII):

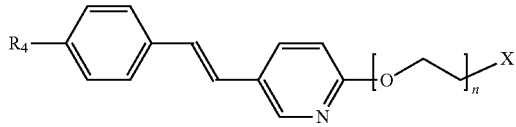

(VII)

$R_4$ and X in Formula (VII) can be independently selected can be selected from H, OH, halogen, substituted or unsubstituted alkyl, substituted or unsubstituted alkoxy, substituted or unsubstituted amino, and substituted or unsubstituted carboxylate; and n can be an integer from 0 to 10. The compound is targeted to any meningiomas in the subject. In one version of the method, before the step of administering to the subject the therapeutically effective amount of the composition, one administers to the subject a detectable amount of the compound of formula (VII) wherein X is replaced with an atom selected from the group consisting of $^{3}H$, $^{11}C$, $^{13}C$, $^{14}C$, $^{13}N$, $^{15}O$, $^{75}Br$, $^{76}Br$, $^{18}F$, $^{19}F$, $^{68}Ga$, $^{82}Rb$, $^{111}In$, $^{123}I$, $^{125}I$, $^{131}I$, $^{201}Tl$, and $^{99m}Tc$, and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In still another aspect, the invention provides a method for treating a meningioma in a subject. The method includes the step of administering to the subject a therapeutically effective amount of a composition including a cytotoxic agent associated with a compound of formula (VIII):

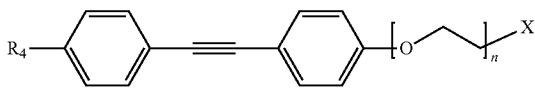

(VIII)

$R_4$ and X in Formula (VIII) can be independently selected can be selected from H, OH, halogen, substituted or unsubstituted alkyl, substituted or unsubstituted alkoxy, substituted or unsubstituted amino, and substituted or unsubstituted carboxylate; and n can be an integer from 0 to 10. The compound is targeted to any meningiomas in the subject. In one version of the method, before the step of administering to the subject the therapeutically effective amount of the composition, one administers to the subject a detectable amount of the compound of formula (VIII) wherein X is replaced with an atom selected from the group consisting of $^{3}H$, $^{11}C$, $^{13}$, $^{14}C$, $^{13}N$, $^{15}O$, $^{75}Br$, $^{76}Br$, $^{18}F$, $^{19}F$, $^{68}Ga$, $^{82}Rb$, $^{111}In$, $^{123}I$, $^{125}I$, $^{131}I$, $^{201}Tl$, and $^{99m}Tc$, and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In yet another aspect, the invention provides a method for treating a meningioma in a subject. The method includes the step of administering to the subject a therapeutically effective amount of a composition including a cytotoxic agent associated with a compound of formula (IX):

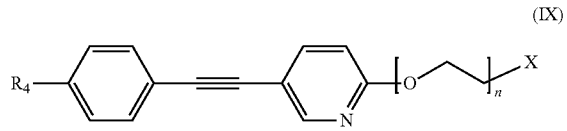

(IX)

R₄ and X in Formula (IX) can be independently selected can be selected from H, OH, halogen, substituted or unsubstituted alkyl, substituted or unsubstituted alkoxy, substituted or unsubstituted amino, and substituted or unsubstituted carboxylate; and n can be an integer from 0 to 10. The compound is targeted to any meningiomas in the subject. In one version of the method, before the step of administering to the subject the therapeutically effective amount of the composition, one administers to the subject a detectable amount of the compound of formula (IX) wherein X is replaced with an atom selected from the group consisting of $^{3}H$, $^{11}C$, $^{13}C$, $^{14}C$, $^{13}N$, $^{15}O$, $^{75}Br$, $^{76}Br$, $^{18}F$, $^{19}F$, $^{68}Ga$, $^{82}Rb$, $^{111}In$, $^{123}I$, $^{125}I$, $^{131}I$, $^{201}Tl$, and $^{99m}Tc$, and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In still another aspect, the invention provides a method for treating a meningioma in a subject. The method includes the step of administering to the subject a therapeutically effective amount of a composition including a cytotoxic agent associated with a compound of formula (X):

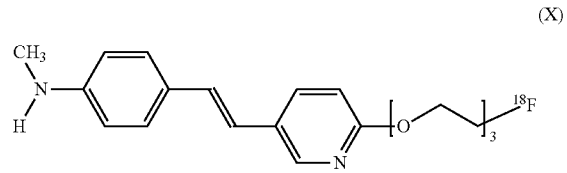

(X)

In one version of the method, before the step of administering to the subject the therapeutically effective amount of the composition, one administers to the subject a detectable amount of the compound of formula (X), and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In yet another aspect, the invention provides a method for treating a meningioma in a subject. The method includes the step of administering to the subject a therapeutically effective amount of a composition including a cytotoxic agent associated with a compound of formula (XI):

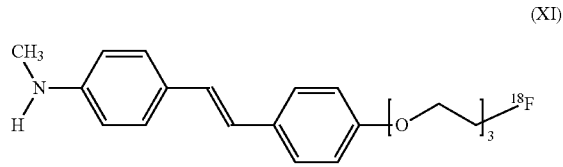

(XI)

The compound is targeted to any meningiomas in the subject. In one version of the method, before the step of administering to the subject the therapeutically effective amount of the composition, one administers to the subject a detectable amount of the compound of formula (XI), and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In still another aspect, the invention provides a method for treating a meningioma in a subject. The method includes the step of administering to the subject a therapeutically effective amount of a composition including a cytotoxic agent associated with a compound of formula (XII):

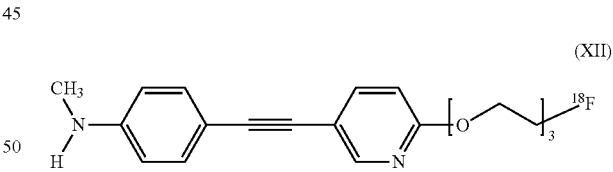

(XII)

The compound is targeted to any meningiomas in the subject. In one version of the method, before the step of administering to the subject the therapeutically effective amount of the composition, one administers to the subject a detectable amount of the compound of formula (XII), and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In yet another aspect, the invention provides a method for treating a meningioma in a subject. The method includes the step of administering to the subject a therapeutically effective amount of a composition including a cytotoxic agent associated with a compound of formula (XIII):

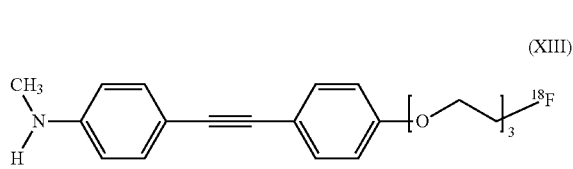

(XIII)

The compound is targeted to any meningiomas in the subject. In one version of the method, before the step of administering to the subject the therapeutically effective amount of the composition, one administers to the subject a detectable amount of the compound of formula (XIII), and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In still another aspect, the invention provides a method for treating a meningioma in a subject. The method includes the step of administering to the subject a therapeutically effective amount of a composition including a cytotoxic agent associated with a compound of formula (XIV):

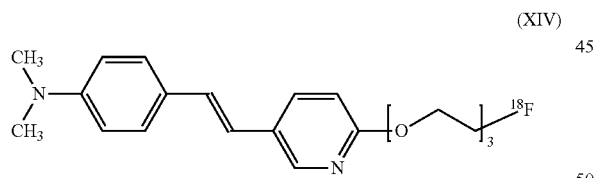

(XIV)

The compound is targeted to any meningiomas in the subject. In one version of the method, before the step of administering to the subject the therapeutically effective amount of the composition, one administers to the subject a detectable amount of the compound of formula (XIV), and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In yet another aspect, the invention provides a method for treating a meningioma in a subject. The method includes the step of administering to the subject a therapeutically effective amount of a composition including a cytotoxic agent associated with a compound of formula (XV):

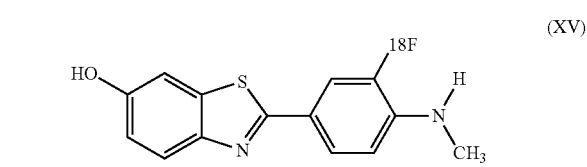

(XV)

The compound is targeted to any meningiomas in the subject. In one version of the method, before the step of administering to the subject the therapeutically effective amount of the composition, one administers to the subject a detectable amount of the compound of formula (XV), and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In yet another aspect, the invention provides a method for treating a meningioma in a subject. The method includes the step of administering to the subject a therapeutically effective amount of a composition including a cytotoxic agent associated with a compound of formula (XVI):

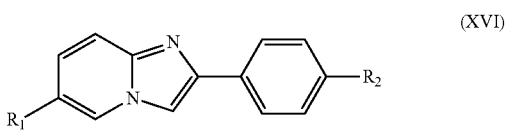

(XVI)

The compound is targeted to any meningiomas in the subject. $R_1$ and $R_2$ in Formula (XVI) can be independently selected from H, OH, halogen, substituted or unsubstituted alkyl, substituted or unsubstituted alkoxy, substituted or unsubstituted amino, and substituted or unsubstituted carboxylate. In one version of the method, before the step of administering to the subject the therapeutically effective amount of the composition, one administers to the subject a detectable amount of the compound of formula (XVI) wherein at least one of the atoms in $R_1$ or $R_2$ is replaced with $^3$H, $^{11}$C, $^{13}$C, $^{14}$C, $^{13}$N, $^{15}$O, $^{75}$Br, $^{76}$Br, $^{18}$F, $^{19}$F, $^{68}$Ga, $^{82}$Rb, $^{111}$In, $^{123}$I, $^{125}$I, $^{131}$I, $^{201}$Tl, and $^{99m}$Tc, and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof.

In yet another aspect, the invention provides a method for treating a meningioma in a subject. The method includes the step of administering to the subject a therapeutically effective amount of a composition including a cytotoxic agent associated with a compound of formula (XVII):

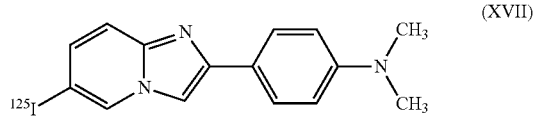 [SMILES: CN(C)c1ccc(-c2cn3cc([125I])ccc3n2)cc1]

The compound is targeted to any meningiomas in the subject. In one version of the method, before the step of administering to the subject the therapeutically effective amount of the composition, one administers to the subject a detectable amount of the compound of formula (XVII), and then one acquires an image to detect the presence or absence of any meningiomas in the subject, and if the presence of any meningiomas is detected in the subject, the step of administering to the subject the therapeutically effective amount of the composition is performed. The step of acquiring the image can be performed using an imaging method selected from positron emission tomography imaging, single photon emission computed tomography imaging, positron emission tomography with concurrent computed tomography imaging, positron emission tomography with concurrent magnetic resonance imaging, single photon emission computed tomography with concurrent computed tomography imaging, or any combination thereof. Formula (XVII) 6-iodo-2-[4'-(N,N-dimethylamino)phenyl]imidazo[1,2-a]pyridine (IMPY), which has structural similarity to the compound of Formula (V) is used in SPECT imaging instead of PET imaging. IMPY and similar molecules could be used to treat meningiomas, such as $^{123}$I-IMPY and $^{131}$I-IMPY.

In still another aspect, the invention provides a composition for treating a meningioma in a subject. The composition includes a cytotoxic agent associated with a compound of any of Formulas (I) to (XVII) above wherein the substituents of each of the Formulas (I) to (XVII) are as described above. The compound is targeted to any meningiomas in the subject.

After administration of the composition of the invention and after a predetermined time period has past, one can administer to the subject a detectable amount of any of the compounds of Formulas (I) to (XVII) above, and then one can acquire an image using the imaging methods noted above to detect any changes in any of the meningiomas in the subject.

Thus, the invention provides a method for treating a meningioma in a subject using a composition including a cytotoxic agent associated with a phenylbenzothiazole derivative or a stilbene derivative or a biphenylalkyne derivative or an imidazo[1,2-a]pyridine derivative chosen from any of the compounds of Formulas (I) to (XVII) above. In the version of the method in which an image is acquired before administering the composition, the image can indicate the presence or absence of any meningiomas in the subject. The presence of any meningiomas in the subject can be indicated by an image in which meningiomas showed activity of the compound of any of Formulas (I) to (XVII) greater than normal adjacent tissues imaged. In any of the above methods, the presence of any meningiomas in the subject can be indicated by a brain image in which meningiomas showed activity of the compound of any of Formulas (I) to (XVII) greater than any other intracranial tumors imaged. In any of the above methods, the presence of any meningiomas in the subject can be indicated by a brain image in which meningiomas showed activity of the compound of any of Formulas (I) to (XVII) greater than any metastases, pituitary macroadenomas, schwannomas, or ependymomas imaged. In any of the above methods, the presence of any meningiomas in the subject can be indicated by an image in which meningiomas showed activity of the compound of any of Formulas (I) to (XVII) greater than any metastases imaged.

It is one advantage of the invention to provide a composition and method for treating a meningioma in a subject. There are no current drugs to treat meningiomas. There are no currently known specific targets in meningiomas against which to design a drug. Surgery is 80-95% effective, invasive with risk of morbidity, and many tumors can not be treated with surgery. Radiation is about 90% effective, but limited to smaller tumors and has side effects. Radiation and surgery get more difficult, less successful and have higher complications if repeated. Drug therapy using the compositions and methods according to the invention can be added to radiation and/or surgery, or used alone.

These and other features, aspects, and advantages of the present invention will become better understood upon consideration of the following detailed description, drawings, and appended claims.

DETAILED DESCRIPTION OF THE INVENTION

Figure 1:
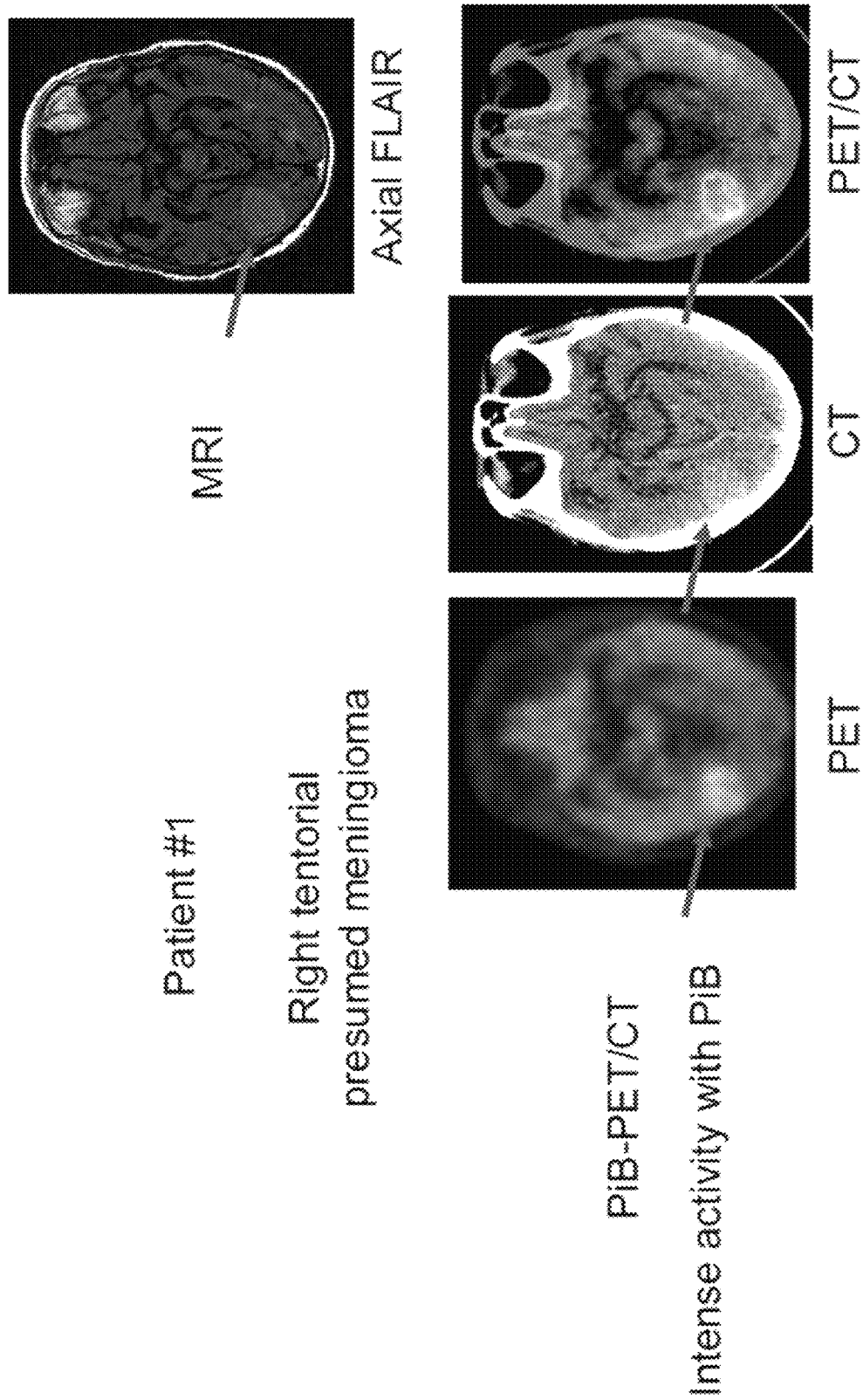
FIG. 1 shows axial images of a brain of a patient obtained using MRI as well as PET/CT using the compound of formula (V). The MRI showed a mass along the right tentorium cerebella, a presumed meningioma, and the combination of PET and CT images showed intense activity with the compound of formula (V) at the meningioma.

The method of the invention exploits the ability of phenylbenzothiazole derivatives or stilbene derivatives or biphenylalkyne derivatives or imidazo[1,2-a]pyridine derivatives to cross the blood brain barrier in vivo and to accumulate in a meningioma. The invention provides a method for treating a meningioma in a subject using a composition of the invention including a cytotoxic agent associated with a phenylbenzothiazole derivative or a stilbene derivative or a biphenylalkyne derivative such as the compounds of Formulas (I) to (XVII) above. The method for treating a meningioma includes the step of administering to the subject a therapeutically effective amount of the composition.

One can first determine the presence (if any) and location of a meningioma at a part (e.g., brain) of the body of a subject by administering a detectable amount of a radiolabeled phenylbenzothiazole derivative or a stilbene derivative or a biphenylalkyne derivative or an imidazo[1,2-a]pyridine derivative chosen from the compounds of Formulas (I) to (XVII) above to a subject. A "detectable amount" means that the amount of the detectable compound that is administered is sufficient to enable detection of accumulation of the compound in a meningioma by a medical imaging technique.

In vivo detection of the accumulated compound in the meningioma can be achieved by medical imaging techniques such as positron emission tomography (PET), computed tomography imaging (CT), magnetic resonance imaging (MRI), single-photon emission computed tomography (SPECT) and any combinations thereof. In the radiolabeled phenylbenzothiazole derivative or stilbene derivative or biphenylalkyne derivative or an imidazo[1,2-a]pyridine derivative chosen from the compounds of Formulas (I) to (XVII) above, the type of medical imaging device is a factor in selecting a given label. For instance, the isotopes $^{3}H$, $^{11}C$, $^{13}C$, $^{14}C$, $^{75}Br$, $^{76}Br$, $^{18}F$, $^{19}F$, $^{68}Ga$, $^{111}In$, $^{123}I$, $^{125}I$, $^{131}I$, and $^{99m}Tc$ are particularly suitable labels for in vivo imaging in the methods of the invention. The type of medical imaging device used will guide the selection of the isotope. For PET detection, the radiolabel will be a positron-emitting radionuclide which will annihilate to form two gamma rays which will be detected by the PET camera. For SPECT detection, the chosen radiolabel will produce minimal if any particulate emission, but will produce a large number of photons.

Concurrent use of two or more of the medical imaging techniques such as PET, CT, MRI, and SPECT can be advantageous in the method of the invention. For example, PET images can demonstrate better correlation to patient anatomy on a CT taken at the time of PET than to patient anatomy on a separate CT (usually taken before the PET image). By using a PET and CT taken back to back with the patient in the same position in the method of the invention, the risk of errors due to motion can be reduced.

For purposes of in vivo imaging, the type of detection instrument available is a major factor in selecting a given label. For instance, $^{19}F$ or $^{13}C$ are suitable for MRI; $^{18}F$, $^{11}C$, $^{13}N$, $^{15}O$, $^{75}Br$, $^{76}Br$, $^{82}Rb$ are suitable for PET; and $^{111}In$, $^{123}I$, $^{125}I$, $^{131}I$, $^{201}Tl$ and $^{99m}Tc$ are suitable for SPECT imaging. $^{3}H$ or $^{14}C$ are suitable for in vitro imaging studies.

Administration to the patient of a pharmaceutical composition including a radiolabeled phenylbenzothiazole derivative or stilbene derivative or biphenylalkyne derivative or an imidazo[1,2-a]pyridine derivative chosen from the compounds of Formulas (I) to (XVII) above for in vivo detection of the accumulated compound in the meningioma can be accomplished intravenously, intraarterially, intrathecally, intramuscularly, intradermally, subcutaneously, or intracavitary. Dosage can vary from 0.001 µg/kg to 10 µg/kg. In the method of the invention, sufficient time is allowed after administration such that the radiolabeled phenylbenzothiazole derivative or stilbene derivative or biphenylalkyne derivative or imidazo[1,2-a]pyridine derivative can accumulate in any meningioma.

We have discovered that the compound of formula (V) above accumulates within meningiomas and recurrent meningiomas. We have also shown that meningiomas and recurrent meningiomas can be diagnosed using positron emission tomography using the compound of formula (V) and related radiolabeled phenylbenzothiazole derivatives.

One non-limiting example method of imaging involves the use of an intravenous injectable molecule such as the compound of formula (V). In the compound of formula (V), a positron emitting (i.e. radioactive) $^{11}$carbon atom gives off a positron, which subsequently annihilates and gives off coincident gamma radiation. This high energy gamma radiation is detectable outside the body through the use of positron emission tomography imaging, or positron emission tomography concurrent with computed tomography imaging (PET/CT). With PET/CT, the location of the injected and subsequently accumulated molecules of Formula (V) within the body can be identified. Our discovery shows that meningiomas accumulate molecules of Formula (V), and that meningiomas are detectable by PET/CT. Our data suggests that other tumors common to the meninges, such as schwannomas, do not accumulate molecules of Formula (V). Since other tumors may not accumulate molecules of Formula (V), PET/CT using the compound of formula (V) can help differentiate meningiomas from other types of tumors.

The compound of formula (V), Pittsburgh compound B (PiB), is a benzothiazole derivative developed as a positron emission tomography (PET) imaging agent. PiB was specifically designed to bind to amyloid plaques in the brains of patients with Alzheimer disease. (See, Mathis C A, Wang Y, Holt D P, Huang G F, Debnath M L, Klunk W E, "Synthesis and evaluation of 11C-labeled 6-substituted 2-arylbenzothiazoles as amyloid imaging agents", *J Med Chem* 2003; 46:2740-54). PiB is an analogue of Thioflavin-T, a fluorescent tissue stain that is commonly used to diagnose Alzheimer disease on autopsy brain tissue.

Once the presence of a meningioma at a part (e.g., brain) of the body of a subject is determined, the meningioma can be treated with a composition of the invention including a cytotoxic agent associated with a phenylbenzothiazole derivative or a stilbene derivative or a biphenylalkyne derivative or an imidazo[1,2-a]pyridine derivative such as the compounds of Formulas (I) to (XVII) above. The method for treating a meningioma includes the step of administering to the subject a therapeutically effective amount of the composition.

A "therapeutically effective amount" means an amount of a composition that, when administered to a subject for treating a disease, is sufficient to effect such treatment for the disease. The "therapeutically effective amount" will vary depending on the composition, the disease state being treated, the severity or the disease treated, the age and relative health of the subject, the route and form of administration, the judgment of the attending medical or veterinary practitioner, and other factors. Those skilled in the art are readily able to determine therapeutically effective amount by administering a composition of the invention to a subject in increasing amounts until the growth of meningioma is decreased or stopped. The rate of growth can be assessed using imaging as described herein. The composition of the invention can be administered to a subject at dosage levels in the range of about 0.1 to about 1,000 milligrams per day.

For a normal human adult having a body weight of about 70 kilograms, a dosage in the range of about 0.01 to about 100 milligrams per kilogram of body weight per day can be sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

For purposes of the present invention, "treating" or "treatment" describes the management and care of a patient for the purpose of combating the disease, condition, or disorder. The terms embrace both preventative, i.e., prophylactic, and palliative treatment. Treating includes the administration of a composition of the present invention to prevent the onset of the symptoms or complications, alleviating the symptoms or complications, or eliminating the disease, condition, or disorder.

A "subject" is a mammal, preferably a human, and most preferably a human suspected of a meningioma. The form in which the composition is administered to the subject is not critical; the active composition need only reach the meningioma, directly or indirectly. For example, the composition of the invention can be administered directly to the meningioma, to a tissue comprising the meningioma, a body fluid that contacts the meningioma, or a body location from which the composition can diffuse or be transported to the meningioma.

The composition can be administered alone or as part of a pharmaceutically acceptable composition. The relative amounts of the active composition, a pharmaceutically acceptable carrier, and any additional active ingredients in a pharmaceutical composition of the invention will vary, depending upon the identity, size, and condition of the human treated and further depending upon the route by which the composition is to be administered. Other pharmaceutically active compounds can be selected to treat the same disease as the composition of the invention or a different disease.

A composition of the invention, optionally comprising other pharmaceutically active compounds, can be administered to a subject parenterally, for example, intravenously, intramuscularly, subcutaneously, intracerebrally or intrathecally. Compositions suitable for parenteral injection comprise the composition of the invention combined with a pharmaceutically acceptable carrier such as physiologically acceptable sterile aqueous or nonaqueous solutions, dispersions, suspensions, or emulsions. Examples of suitable aqueous and nonaqueous carriers, diluents, solvents, or vehicles include water, isotonic saline, ethanol, and polyols (propylene glycol, polyethylene glycol, glycerol, and the like), and mixtures thereof.

A composition of the invention includes a cytotoxic agent associated with a phenylbenzothiazole derivative or a stilbene derivative or a biphenylalkyne derivative or an imidazo[1,2-a]pyridine derivative such as one of the compounds of Formulas (I) to (XVII) above. The cytotoxic agent can be selected from cytotoxins, chemotherapeutic agents, radiation-emitters, and combinations thereof. A cytotoxic agent is "associated" with one of the compounds of Formulas (I) to (XVII) above if the cytotoxic agent is directly or indirectly, physically or chemically bound to one of the compounds of Formulas (I) to (XVII) above. Non-limiting examples of chemical bonds include covalent bonds, ionic bonds, coordinate bonds, and hydrogen bonds. Indirect bonding can include the use of a group of atoms (i.e., a linker) that chemically links the cytotoxic agent and one of the compounds of Formulas (I) to (XVII) above. Non-limiting examples of physical bonding include physical adsorption and absorption. Having been supplied with the structures of the specific cytotoxic agent and one of the compounds of Formulas (I) to (XVII) above, the cytotoxic agent can be associated with one of the compounds of Formulas (I) to (XVII) above using laboratory techniques.

The cytotoxic agent can be a cytotoxin. Non-limiting examples of cytotoxins include ricin, pseudomonas exotoxin, diphtheria toxin, and combinations thereof.

The cytotoxic agent can be a chemotherapeutic agent. Non-limiting examples of chemotherapeutic agents include alkylating agents, antagonists, plant alkaloids, intercalating antibiotics, enzyme inhibitors, antimetabolites, mitotic inhibitors, growth factor inhibitors, cell cycle inhibitors, enzymes, biological response modifiers, and combinations thereof.

The cytotoxic agent can be a radiation-emitter such as a radioisotope that kills cancer cells. Non-limiting examples of radiation-emitters include phosphorus-32, phosphorus-33, bromine-77, yttrium-88, yttrium-90, molybdenum-99m, technetium-99m, indium-111, indium-131, iodine-123, iodine-124, iodine-125, iodine-131, lutetium-177, rhenium-186, rhenium-188, bismuth-212, bismuth-213, astatine-211, and combinations thereof. Preferably, the radiation-emitter is yttrium-90 or iodine-131.

We have discovered that Pittsburgh compound B (PiB) binds specifically to meningiomas. A radioactive version of PiB (Formula (V)) can be synthesized with a cyclotron using radiochemistry. This radioactive version of PiB is used as a molecular imaging agent, otherwise known as a radiotracer.

When injected into the venous blood of a patient, we have shown that the compound of Formula (V) goes to meningiomas and accumulates there. The compound of Formula (V) gives off radioactivity that radiates out of the body of the injected patient. This radioactivity is detected with scintillation crystals within a Positron Emission Tomography (PET) scanner. In this way we can identify meningiomas within patients on the images produced by the Positron Emission Tomography (PET) scans. By combining the PET scan images with images from a CT scan performed just prior to the PET scan, we can prove that the molecules of the compound of Formula (V) are accumulating within a patient's meningioma. This is because we can see the meningioma on the CT scan images and we can show the radioactivity is coming from the compound of Formula (V) within the meningioma. In patients who also received prior Magnetic Resonance Imaging (MRI) scans, we can also fuse the information from the PET and CT scans to the MRI scan, thus further confirming that the compound of Formula (V) is within the meningioma. This is helpful since meningiomas are very well seen on MRI, especially if intravenous gadolinium contrast is given to enhance the meningioma. Our data shows that when the compound of Formula (V) accumulates in a presumed meningioma, it helps to confirm the diagnosis of meningioma, since other (non-meningioma) tumors do not accumulate the compound of Formula (V).

In addition to showing that the compound of Formula (V) is accumulating within a patient's meningioma, we can also show that the compound of Formula (V) is accumulating to a lesser degree or not at all within other structures in the same patient. Thus, the specificity for the compound of Formula (V) to a meningioma in a given patient can be confirmed. The amount of harmful radiation to the patient as a result of the injection of the compound of Formula (V) and PET/CT imaging is within acceptable limits for diagnostic purposes.

Once the accumulation of the compound of Formula (V) within the meningioma is confirmed with PET imaging, a different version of the compound of Formula (V) containing or carrying a radioactive or otherwise harmful moiety can be injected into the venous blood. This version of the compound of Formula (V) will also accumulate within the meningioma, and less so in other structures, thus delivering a targeted therapy to the meningioma. The compound of Formula (V) and many other similar molecules and amyloid-targeted molecules have been tested for biodistribution and kinetics in animals and people. Most, if not all of them show rapid washout from the body through the liver into the gastrointestinal tract and less so through the kidneys into the urine. The gall bladder may be the normal tissue that receives the highest side effects of a drug therapy, and if so could be surgically removed prior to therapy, induced to constrict with cholecystokinin, or removed after therapy if needed.

If the therapeutic (i.e. cytotoxic agent containing) version of the compound of Formula (V) is radioactive, then a second set of confirmatory images could be created with either PET, planar imaging or single photon emission tomography (SPECT) either alone or in combination with CT. Such imaging could further increase the confidence that this type of therapy is specific to the targeted meningioma.

The compounds of Formulas (I) to (IV) and (VI) to (XVII) may act similarly and accumulate within meningiomas. These compounds could be used in the same way as the compound of Formula (V), for imaging and therapy. The compound of Formula (V) is a benzothiazole derivative of thioflavin-T, originally designed to bind to amyloid-beta. Therefore it is possible that other radiotracers designed to bind to amyloid-beta may also accumulate within meningiomas, and may be useful as imaging and therapeutic agents. These agents include, without limitation, the compound of Formula (X) and the compound of Formula (XI). Derivations of the compound of Formula (V) and amyloid imaging agents labeled with a different radioactive nuclide can be used in planar, SPECT or SPECT/CT imaging in a similar manner to those agents used in PET or PET/CT imaging. Another example is 6-iodo-2-[4'-(N,N-dimethyl-amino)phenyl]imidazo[1,2-a]pyridine (IMPY), which has structural similarity to the compound of Formula (V) and is used in SPECT imaging instead of PET imaging. IMPY and similar molecules could be used to treat meningiomas, such as $^{125}$I-IMPY and $^{131}$I-IMPY.

Figure 6:
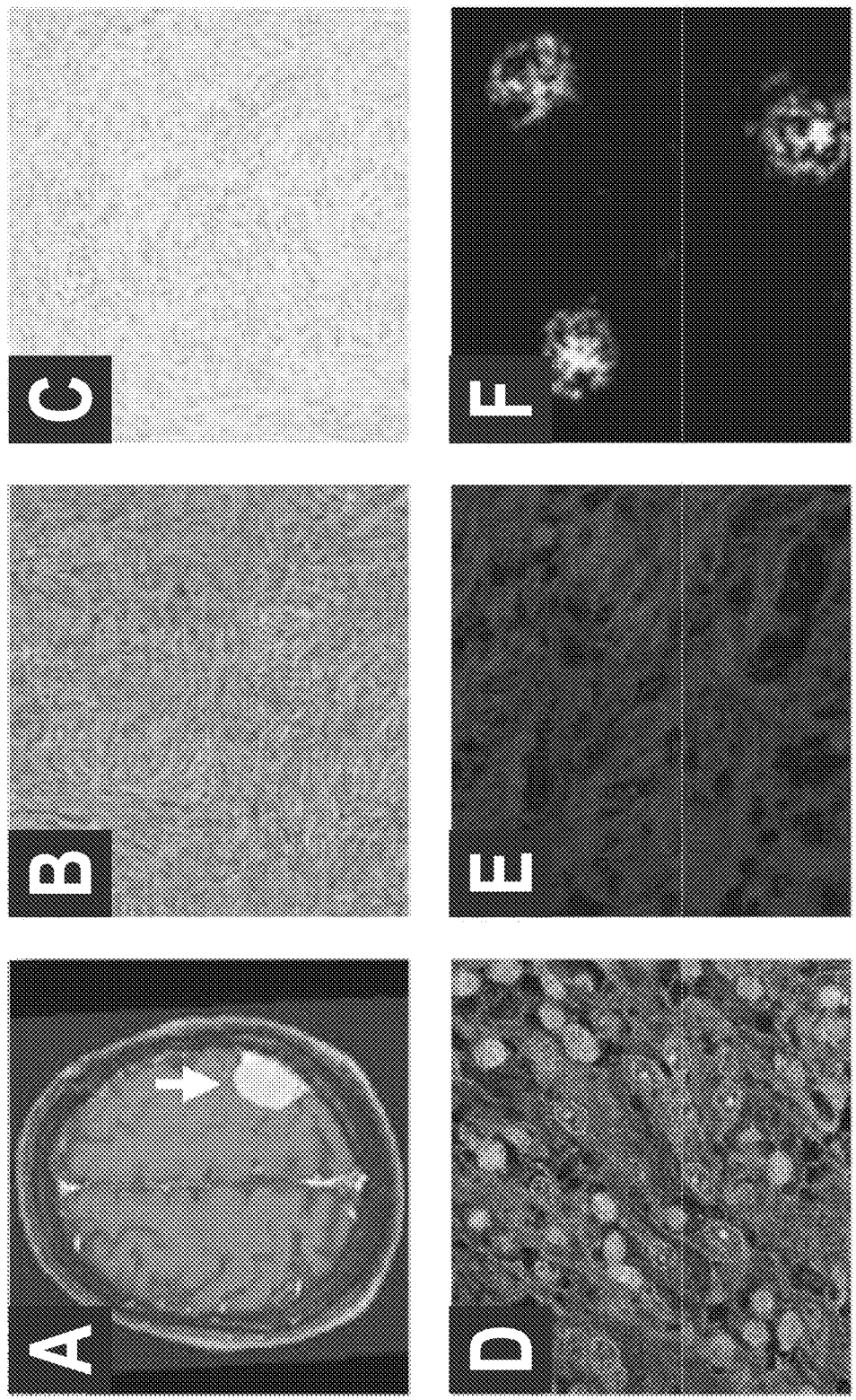
FIG. 6 shows meningioma tissue stains compared to a schwannoma and amyloid plaques in the cerebral cortex.

It has been shown in the work of others, prior to our discovery of the compound of Formula (V) binding to meningiomas, that meningiomas do not contain amyloid-beta. It has also been shown that meningiomas do not contain the proteins tau or alpha-synuclein. Amyloid-beta, tau and alpha-synuclein are the dominant/common components of the amyloid-beta neuritic plaques and neurofibrillary tangles seen in the brains of those diagnosed with Alzheimer's dementia. These plaques and tangles are what Thioflavin-T and the compound of Formula (V) binds to in the gray matter of patents with Alzheimer's disease, and perhaps those who are at risk to develop Alzheimer's disease. In addition, meningiomas have been shown to not express the gene that creates the alpha-synuclein protein, in that meningiomas lack mRNA for alpha-synuclein. In addition, tissue stains that target a wide array of amyloid substances that include, but are not limited to, amyloid-beta, do not stain meningiomas. Congo red is such a stain that binds a wide array of types of amyloid. Meningiomas have been shown to be negative with congo red staining, implying they lack most types of amyloid. Therefore, this discovery we have made of compound of Formula (V) accumulating within meningiomas was unexpected. Our research confirms the lack of amyloid-beta within meningiomas. We have stained meningioma tumor tissues with antibodies for amyloid-beta, and they are negative. For example, immunohistochemical staining of meningiomas with the mouse monoclonal anti-human beta-amyloid antibody (clone 6F/3D) (available from Leica Biosystems) shows that meningiomas are negative for the presence of beta-amyloid (FIG. 6, panel C).

Our research on tissue sections of meningiomas, confirms our PET imaging findings, showing meningioma tissues accumulate the compound of Formula (V). Meningiomas accumulate the compound of Formula (V) and a highly-fluorescent version of the compound of Formula (V) (wherein a fluorescent CN group is attached to the compound of Formula (V)). This is consistent with our discovery of meningiomas accumulating the compound of Formula (V) when injected into the venous blood stream and imaged with PET. The compound of Formula (V) and the highly-fluorescent version of the compound of Formula (V) accumulate within the meningioma tissues when these tissues are soaked in solutions containing the compound of Formula (V) or the highly-fluorescent version of the compound of Formula (V). The compound of Formula (V) and the highly-fluorescent version of the compound of Formula (V) in tissues of meningiomas can be seen with a fluorescent microscope. One area where the compound of Formula (V) or the highly-fluorescent version of the compound of Formula (V) accumulate is within the nucleus of the cells of the meningiomas. More specifically, they accumulate within the heterochromatin areas and the nucleolus. This is a pattern of staining (or accumulation of the compound of Formula (V)) that may be specific to meningiomas, that has not been described for other tissues types that have been stained with the compound of Formula (V). We do not see this staining pattern within brain cortical gray matter, or white matter for example. Moreover, we do not see this pattern within the cortical gray matter from patients with Alzheimer's disease.

Methods to create therapeutic compositions that bind meningiomas, and do not cross the blood brain barrier may be employed. This could be advantageous, and would avoid interaction of the composition with amyloid-beta that might be present within the brain of some patients. Charged molecules, and larger molecules do not cross the blood brain barrier. Meningiomas reside outside the blood brain barrier.

Candidate therapeutic compositions can be initially evaluated in tissue staining of meningiomas or meningioma cell lines for similarity to the binding pattern and intensity of the compound of Formula (V) or the highly-fluorescent version of the compound of Formula (V). Such compositions include a fluorescent version of the compound of Formula (X), wherein a fluorescent CN group is attached to the compound of Formula (X).

Candidate compositions, with both an imaging and therapeutic version, could be tested in patients with meningiomas. They could also be tested in animal models of meningiomas. Versions of such an animal model has been described in mice, wherein cells from human meningiomas are placed within a mouse and allowed to grow. These can grow in the retroperitoneum or intracranial for example. Alternatively, animal models where meningiomas are induced to develop have been described. Several versions of these mouse models have been published. Meningiomas in humans and animals can be imaged and therefore monitored with MRI, CT, PET/CT, and SPECT/CT.

Successful compositions would be seen accumulating within meningiomas, and less so elsewhere in the body. These compositions would dwell long enough within the meningioma to be able to be imaged and also to be able to deliver the desired therapeutic effect. This effect could be measured by monitoring the size of the tumor on MRI or other imaging before and after delivery of the composition and compared to mice who received no composition, or a sham or inactive version of the composition. MRI can be performed with added benefit of gadolinium enhancement, making the meningioma tumor more conspicuous, even in the animal models. The length of life of the mice could also be monitored, or the time to certain measurable morbid states, and when seen the mice could be euthanized.

Alternatively, the composition could be given in conjunction with surgery and/or radiation. The composition could be preferentially given to human patients in whom no alternative therapy is considered medically feasible, such as those with recurrent meningiomas, those with large meningiomas, or those with meningiomas in difficult locations. Very rarely meningiomas are malignant and can be metastatic. In patients with malignant meningiomas drug therapy could also be tested.

Most meningiomas occur sporadically in older adults. However, drug therapy may be particularly beneficial to patient's with neurofibromatosis type II, a genetic condition. These patients often develop numerous and large meningiomas early in life. Some of these meningiomas require therapy, such as spinal lesions compressing their central nervous system. In patients with numerous meningiomas, like those with neurofibromatosis type II, drug therapy would be particularly useful since it would act systemically.

As an alternative to using a composition including a cytotoxic agent and one of the compounds of Formulas (I) to (XVII) above for therapy, the unique target to which one of the compounds of Formulas (I) to (XVII) is binding within meningiomas could be identified, and targeted with a different molecule, drug, biologic agent or antibody. Such an agent could be made radioactive for imaging purposes, and could be modified to be therapeutic as described above. The identification of that unique target could be performed by many different methods.

Methods to discover the target within meningiomas that one of the compounds of Formulas (I) to (XVII) is binding include, making cDNA library. Meningioma tumor cells or cell lines could be used to create a cDNA library of all the mRNA in the cells. This represents the genes that are active, or those genes that are making proteins. This library can be selectively placed into cDNA delivery agents, such as plasmids, that enter into cells. Cells from something other than a meningioma, can be used as a target for the plasmids. These target cells would then be able to make the mRNA of the gene selected from the meningioma. These cells, each carrying a gene from the meningioma, could be tested to show if they do or do not accumulate one of the compounds of Formulas (I) to (XVII), by staining with one of the compounds of Formulas (I) to (XVII) or a fluorescent version of one of the compounds of Formulas (I) to (XVII). In other words, the cells that received cDNA could then be tested to see if they gain the ability to accumulate one of the compounds of Formulas (I) to (XVII) in a manner similar to meningiomas. Those cells that do gain the ability to accumulate one of the compounds of Formulas (I) to (XVII) may contain cDNA for a gene responsible for a protein to which one of the compounds of Formulas (I) to (XVII) is binding in meningiomas. The cDNA can be removed from these cells and sequenced to discover what specific gene is responsible.

Alternatively, a cell homogenate from meningiomas could be used. These broken up pieces of meningiomas cells and extracellular matrix could be used to bind to one of the compounds of Formulas (I) to (XVII), thus extracting the target substance from the meningiomas.

Alternatively antibodies or other molecules could be used to compete with one of the compounds of Formulas (I) to (XVII) binding to meningiomas. Agents that can compete with one of the compounds of Formulas (I) to (XVII) are likely binding to the same target. Antibodies could be created to an array of targets randomly selected within meningiomas. Once an antibody is selected by this method, the antibody can be used to bind and extract and identify the target from meningioma cells.

EXAMPLES

The following Examples have been presented in order to further illustrate the invention and are not intended to limit the invention in any way.

A compound of formula (V) below was selected for investigation.

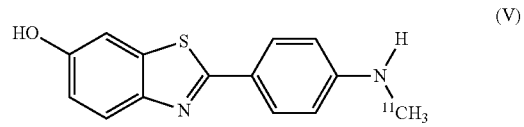

The compound of formula (V) is also known as [N-Methyl-$^{11}C$]$_2$-(4'-methylaminophenyl)-6-hydroxybenzothiazole (CAS Number 566170-04-5) or Pittsburgh compound B (PiB). It can be synthesized using the methods described in U.S. Pat. No. 7,270,800.

Example 1

An Alzheimer's imaging database of two hundred forty-one patients was reviewed. Some of the patients had a history of cognitive impairment that might be due to early Alzheimer's disease and some were normal controls. All patients had been imaged by at least one MRI, as well as by FDG-PET/CT and PET/CT using the compound of formula (V). MRI reports of all patients were reviewed for possible meningiomas and other tumors. Seven patients were found to have the diagnosis of presumed meningioma based on MRI and sometimes also on CT. The diagnostic confidence of the radiologists interpreting the studies varied slightly, depending on factors such as tumor location and previous imaging. Of these seven tumors, six showed intense uptake of the compound of formula (V) on PET/CT. One showed some uptake, but was difficult to evaluate presumably because of its small size (~4 mm. thick). Tumors smaller than 7 millimeters are generally considered too small to be evaluated by PET or PET/CT. This is an excepted limitation of PET or PET/CT as a modality. Our data confirm that meningiomas have a variable uptake on fluorodeoxyglucose (FDG)-PET/CT with four showing no uptake and two showing mild uptake, and one too small to evaluate. None of the meningiomas in the series would be classified as atypical or aggressive based on MRI or CT imaging. One presumed extracranial schwannoma was seen, showing mild uptake on FDG-PET/CT, but no uptake on PET/CT using the compound of formula (V). Other tumors were also seen with little to no uptake of the compound of formula (V).

FIG. 1 shows axial images of a brain of a patient (identified as Patient #1 in FIG. 1) obtained using MRI as well as PET/CT using the compound of formula (V) (identified as PiB in FIG. 1). The MRI showed a mass along the right tentorium cerebelli, a presumed meningioma, and the combination of PET and CT images showed intense activity with PiB at the meningioma.

Figure 2:
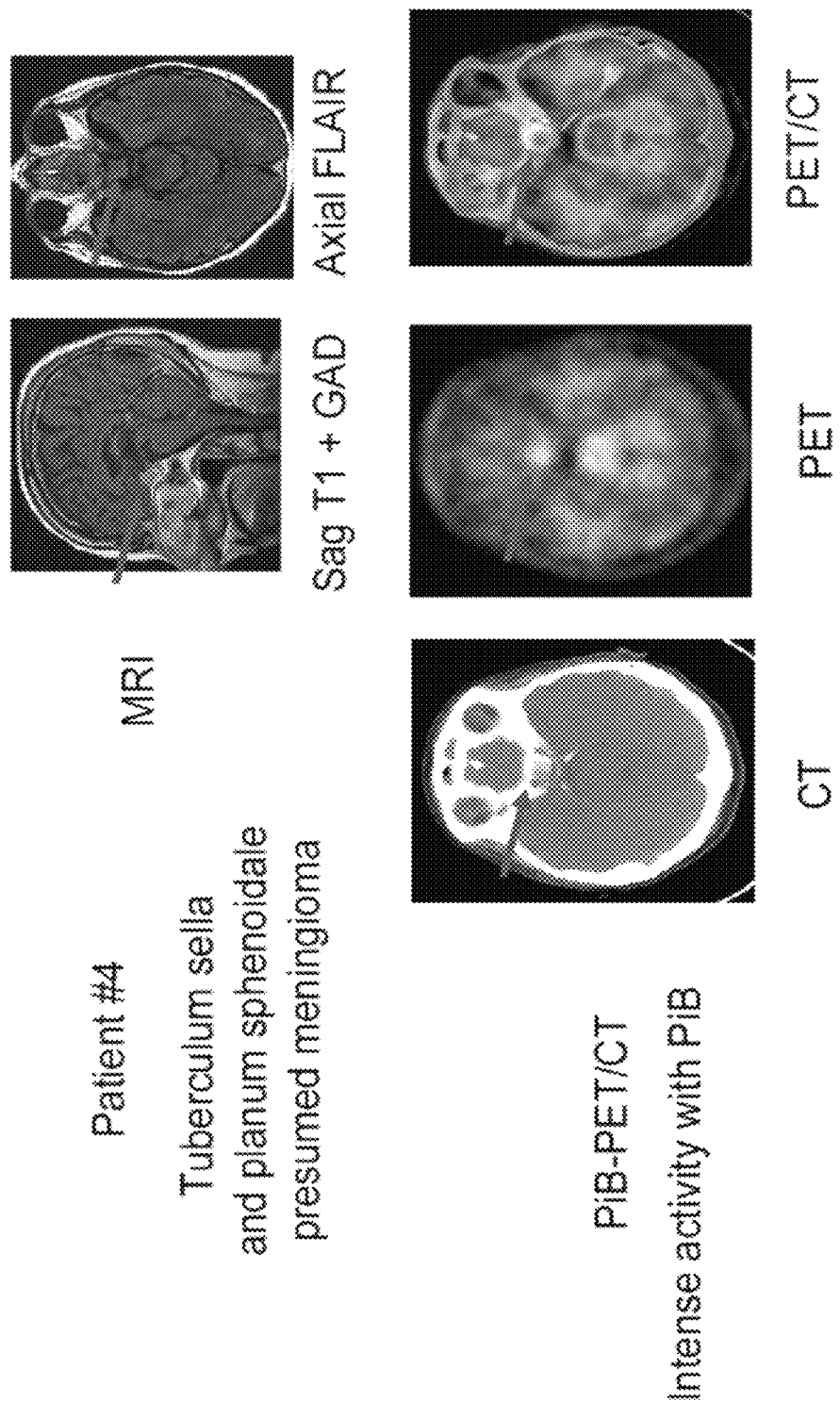
FIG. 2 shows sagittal and axial images of a brain of a patient obtained using MRI as well as PET/CT using the compound of formula (V). The MRI showed a mass along the tuberculum sellae and planum sphenoidale, a presumed meningioma, and the combination of PET and CT images showed intense activity with the compound of formula (V) at the meningioma.

FIG. 2 shows sagittal and axial images of a brain of a patient (identified as Patient #4 in FIG. 2) obtained using MRI as well as PET/CT using the compound of formula (V) (identified as PiB in FIG. 2). The MRI showed a mass along the tuberculum sellae and planum sphenoidale, a presumed meningioma, and the combination of PET and CT images showed intense activity with PiB at the meningioma.

Example 2

In Example 1, we identified six patients with meningiomas >5 millimeters in size that showed positive uptake of the compound of formula (V) on PET/CT. We identified three more patients with four presumed meningiomas. All three patients were imaged by PET-CT using the compound of formula (V), FDG PET-CT and MRI within as part of the ongoing amyloid imaging study. In one patient, there are two meningiomas. One is in the orbit, and is therefore extracranial. This orbital meningioma was previously resected and pathologically shown to be a meningioma in 1969, and pathology was confirmed later at our institution. It has now regrown within the orbit. The other meningioma is along the falx. Both show avid uptake of the compound of formula (V). There were two other patients with a single meningioma with uptake of the compound of formula (V). Therefore, there are a total of ten presumed meningiomas that show uptake of the compound of formula (V) on PET/CT.

Example 3

In Examples 1 and 2, we identified ten patients with meningiomas >5 millimeters in size that showed positive uptake of the compound of formula (V) on PET/CT. We identified three more examples of presumed meningiomas that show activity using the compound of formula (V) on PET-CT, for a total of thirteen. All of these formula (V) avid meningiomas are >5 millimeters in size. We also identified three more presumed meningiomas that showed some positive uptake of formula (V), but were non-diagnostic due to common limitations of PET/CT imaging. One of these non-diagnostic presumed meningiomas was too small to evaluate by PET or PET/CT. One of these non-diagnostic presumed meningiomas was necrotic/cystic centrally with a 4 millimeter rim of tumor, and is therefore effectively also too small to evaluate by PET or PET/CT. The other of these non-diagnostic presumed meningiomas was only seen in the last 2 slices of PET data, an area considered to be uninterpretable. In addition, this patient moved during the exam, causing artifact. Therefore, our data show all thirteen out of thirteen presumed meningiomas that were >5 millimeters in size and within the diagnostic field of view of PET-CT showed positive uptake with formula (V) and were positive on PET/CT imaging. One of these patients with a presumed meningioma was imaged two times with formula (V), with many months in between, and showed the same positive results. Therefore, we have shown that imaging of meningiomas with formula (V) and PET/CT is reproducible. In addition to presumed meningiomas we found within this group of patients 25 different types of tumors and non-neoplastic lesions, including a presumed schwannoma, hamartoma, ependymoma and pituitary adenoma, which all showed only background uptake or no uptake with formula (V) and were not positive on PET/CT. Therefore, we have shown that imaging of meningiomas with formula (V) and PET/CT is specific.

Example 4

Summary of Example 4

Intracranial metastases and other tumors often mimic the appearance of common benign meningiomas on CT and MRI, leading to delayed therapy, misdiagnoses and surgical biopsies. Pittsburgh compound B (PiB) is a positron emission tomography (PET) imaging radiotracer. PiB was designed to bind beta-amyloid in the brain and similar compounds are in FDA trials for use as imaging biomarkers of Alzheimer's disease. Unexpectedly, we observed that meningiomas accumulate PIB. We evaluated if meningiomas could be diagnosed with PiB PET/CT imaging, and furthermore, whether such imaging might be due to amyloid within meningiomas. 834 adult patients who underwent MRI, F18-FDG PET/CT and C11-PiB PET/CT imaging as part of the Mayo Clinic Study of Aging were retrospectively reviewed. Presumed meningiomas and other intracranial tumors detected on MRI were identified and all available imaging was reviewed. Tumor tissue sections were stained with PiB, highly fluorescent 6-CN-PIB, and anti-amyloid antibodies. All 16 meningiomas identified by strict imaging criteria showed PiB activity greater than normal adjacent tissues. All other intracranial tumors imaged, including metastases, pituitary macroadenomas, schwannomas and an ependymoma, showed PiB activity equal or less than normal adjacent tissue. Tissue sections from meningiomas stained brightly positive with PiB, showing a distinct staining pattern, but stained negative with amyloid specific antibodies. It was concluded that meningiomas take up PiB, and can therefore be identified with PET. This finding could lead to a substantial advance in the medical care of people with meningioma-like brain tumors. Tissue stains suggest that PiB is binding to something other than amyloid within meningiomas.

Methods

Patient Selection

The radiologic interpretations of MRI, CT and FDG PET/CT scans from a population of 834 people who participated in the population-based Mayo Clinic Study of Aging (MCSA) from March 2006 through September 2011 were reviewed for the presence of tumors or other brain lesions. (See, Kantarci K, Lowe V, Przybelski S A, et al., "Magnetic resonance spectroscopy, {beta}-amyloid load, and cognition in a population-based sample of cognitively normal older adults", *Neurology* 2011; 77:951-8; and Roberts R O, Geda Y E, Knopman D S, et al., "The Mayo Clinic Study of Aging: design and sampling, participation, baseline measures and sample characteristics", *Neuroepidemiology* 2008; 30:58-69.) Participants were randomly selected for recruitment in the MCSA from a population of older adult residents of Olmsted County, Minn., USA. Those with neurological, psychological or systemic illnesses were not excluded. Individuals with dementia, or those unable to be imaged for medical reasons were excluded. All patients were imaged with C11-PiB PET/CT, F18-FDG PET/CT and noncontrast MRI at least once as part of the study. Any additional patient imaging and clinical history was then reviewed.

Tumors found in any of the subjects were then categorized as possible meningiomas or non-meningiomas based on the reading of the reporting neuroradiologist. Possible meningiomas were further reviewed as a group. A more strict set of criteria were applied to select a subset of the possible meningiomas that were designated "high-likelihood meningiomas" for further analysis and were defined by (1) tumors that were confirmed to be enhancing on diagnostic MRI (obtained separately for clinical purposes) and (2) tumors that had greater than two years of follow-up imaging confirming no growth or slow growth (1-2 mm per year). When the lead diagnosis of the identified tumor was metastasis, the diagnosis was confirmed by biopsy or autopsy. All tumors smaller than 5 mm thick were excluded, given they fall below the generally accepted lower limits of PET/CT resolution.

Imaging

PET imaging was performed as part of the Mayo Clinic Study of Aging as previously described. (See Kantarci K, Lowe V, Przybelski S A, et al., "Magnetic resonance spectroscopy, {beta}-amyloid load, and cognition in a population-based sample of cognitively normal older adults", *Neurology* 2011; 77:951-8.) PiB PET/CT, then FDG PET/CT were performed on the same day. PET/CT imaging was performed on a 690XT or DRX PET/CT tomograph (GE Healthcare). The PET sinograms were reconstructed using a fully-3D OSEM algorithm into a 30 cm field of view; the pixel size was 1.2 mm and the slice thickness was 3.27 mm (DRX) or 1.96 mm (690XT). CT imaging was obtained immediately prior to PET acquisition and used for attenuation correction. Cerebral PiB retention, a marker of amyloid deposition, was measured as previously described. (See Kantarci K, Lowe V, Przybelski S A, et al. "Magnetic resonance spectroscopy, {beta}-amyloid load, and cognition in a population-based sample of cognitively normal older adults", *Neurology* 2011; 77:951-8.)

Noncontrast MRI studies were performed as part of the Mayo Clinic Study of Aging using a standard research protocol as previously described. (See Kantarci K, Lowe V, Przybelski S A, et al., "Magnetic resonance spectroscopy, {beta}-amyloid load, and cognition in a population-based sample of cognitively normal older adults", *Neurology* 2011; 77:951-8.) Additional imaging obtained for clinical purposes was also reviewed, including contrast enhanced MRI exams when available. MRI images were fused with PET/CT data when necessary to confirm anatomic registration of PET activity with brain tumors. Fusion was performed with a point-based rigid registration method using OsiriX Open-Source PACS Workstation, 64-bit version 3.9.4 (Pixmeo).

Materials

C11-PiB and F18-FDG were produced on-site in a Mayo Clinic cyclotron facility. Production and quality control methods are described at Lowe V J, Kemp B J, Jack C R, Jr., et al., "Comparison of 18F-FDG and PiB PET in cognitive impairment", *Journal Of Nuclear Medicine*: official publication, Society of Nuclear Medicine 2009; 50:878-86. 6-CN-PiB was synthesized as previously described at Ikonomovic M D, Klunk W E, Abrahamson E E, et al., "Postmortem correlates of in vivo PiB-PET amyloid imaging in a typical case of Alzheimer's disease", *Brain: A Journal Of Neurology* 2008; 131:1630-45. Non-radioactive PiB, used for tissue staining, was purchased from ABX. NCL-B-Amyloid anti-amyloid antibody was purchased from Leica.

Tumor Selection for Tissue Staining

The Department of Pathology, Mayo Clinic Rochester Tumor Tissue Registry, contains tumor samples procured by autopsy and surgery. Meningiomas, brain metastases and other tumors were identified by searching CoPath, a Mayo Clinic electronic pathology database of tumors collected since 1982. Tumor type was confirmed by viewing H&E stained slides under a light microscope.

Tissue Stains

Fresh cut 5 μm thick sections were used. Each staining run included normal brain and Alzheimer diseased brain as controls. Fluorescent tissue staining and microscopy was performed similar to methods previously described at Ikonomovic M D, Klunk W E, Abrahamson E E, et al., "Postmortem correlates of in vivo PiB-PET amyloid imaging in a typical case of Alzheimer's disease", *Brain: A Journal Of Neurology* 2008; 131:1630-45. Meningioma and other brain tumor sections were stained with 100 nM CN-PiB, 100 nM of unlabeled PiB or with saline alone as a negative control. The staining protocol was as follows: deparaffinization and rehydration, 0.25% $KMnO_4$ incubation, water wash, 1% $K_2S_2O_5$/1% Oxalic Acid incubation, water wash, PBS wash, 6-CN-PiB/PiB/saline incubation, PBS wash, NaCl, $K_2HPO_4$, and $KH_2PO_4$ incubation, water wash, mount coverslip, and storage at 4° C. in the dark until imaged. Slides were imaged within five days of staining. Immunohistochemical staining of meningiomas for beta amyloid protein was performed using NCL-B-Amyloid mouse anti-human antibody per standard clinical protocol.

Fluorescent Microscopy

Tissue stain images were obtained on a Zeiss 510 confocal microscope with excitation at 405 nm, a 420-480 bandpass filter, and the laser set at 15% power.

Images were obtained with a C-Apochromat 40×/1.2 W lens.

Light Microscopy

Digital light microscopy images were obtained with NanoZoomer Digital Pathology (Hamamatsu). Color digital images were produced via a 3-CCD digital camera. WebSlide Enterprise software (Olympus) was used to process the digital images.

Results

PiB PET/CT of Tumors and Lesions Identified on Imaging of the Head

Excluding tiny tumors, a total of 24 possible meningiomas were identified in the population of 834 patients. Of those 24 possible meningiomas, 16 tumors in 15 patients met our strict imaging criteria for high-likelihood meningiomas. All 16 meningiomas were clearly diagnostically positive on PiB PET/CT imaging. Among these 16 tumors, the average SUVmax (by body weight) was 2.2 (range 1.4-3.6). This level of activity was well above the average background PiB activity in the surrounding cerebrospinal fluid (SUVmax 0.2), and the average PiB activity of nearby normal grey matter and bone (SUVmax 1.1 and 0.6 respectively). Of note, 8 of these patients (53%) had high PiB retention in cerebral grey matter per previously described criteria (See Kantarci K, Lowe V, Przybelski S A, et al., "Magnetic resonance spectroscopy, {beta}-amyloid load, and cognition in a population-based sample of cognitively normal older adults", *Neurology* 2011 77:951-8.), but this did not interfere with the identification of any meningiomas (for example, see FIG. 3).

Figure 3:
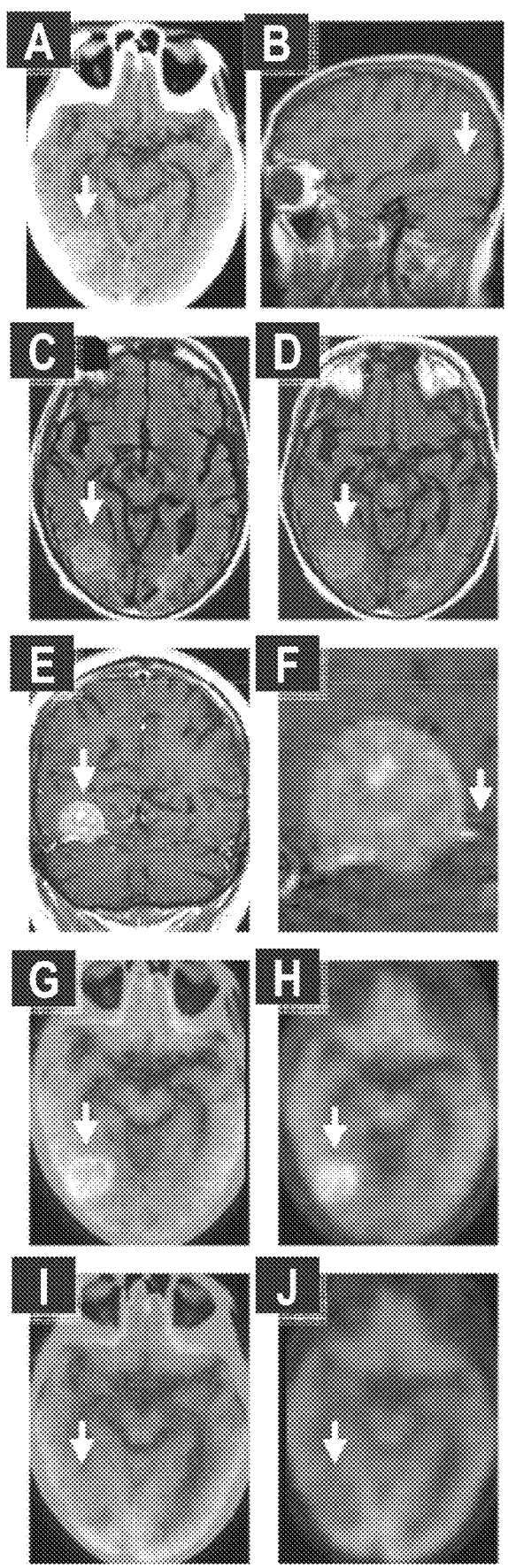
FIG. 3 shows axial, sagittal and coronal images of a brain of a patient obtained using CT and MRI, as well as PET/CT using the compound of formula (V). The images show meningioma arising from the meninges of the right tentorium and compressing the right posterior temporal lobe.

FIG. 3 shows a classic meningioma positive on PiB PET/CT. A 2.6 cm thick meningioma arising from the meninges of the right tentorium and compressing the right posterior temporal lobe (arrows). This tumor shows increased density on non-contrast CT (Panel A), low signal on T1-weighted MRI images (Panel B; sagittal), high signal on T2-weighted images (Panels C&D), uniform enhancement with an enhancing dural tail (Panels E&F coronal: arrow on F shows dural tail), and very slow growth over greater than 3 years (Panels C&D). This meningioma was highly active on PiB PET/CT (Panels G&H) with a SUVmax of 2.8. Of note, this patient had increased PiB activity in the cerebral grey matter indicative of amyloid deposition. This meningioma showed only trace FDG activity (Panels I&J).

The meningiomas had the following MRI and CT imaging characteristics: average thickness 1.4 cm (range 0.5-2.6); 11 had a dural tail sign; 10 showed slow growth; 4 were calcified; 2 induced hyperostosis of overlying bone; and 1 was partially cystic. Meningiomas were found adjacent to the peripheral cerebrum and cerebellum, tuberculum sellae, sella turcica, falx, internal auditory canal, cerebellar pontine angle, and within the lateral ventricle. Seven meningiomas had moderate to high FDG activity. The meningiomas were imaged with an average of 6.8 MRI scans and 1.0 diagnostic CT scans over an average of 6.3 years (range 2.5-12.3). One person had 2 meningiomas. One person with a 2.0 cm thick meningioma had focused irradiation 1 month prior to PiB PET/CT imaging, but still had PiB activity (SUVmax 3.6), after which the tumor appeared to stop growing on follow-up MRI 1 year later. Two patients were imaged with PiB PET/CT more than once with stable or increasing SUVmax of their meningioma.

The population with meningiomas was similar to the general population studied. The general population were adult patients, average age 78.4 years (standard deviation +/−7.1). 42% of the participants were women, and 32% had mild cognitive impairment. Those with meningiomas had an average age of 80.1 years (range 71-95). Eight (53%) of those with meningiomas were female, and 5 (33%) had mild cognitive impairment. Fourteen patients (93%) had neurology and/or neurosurgery consultation for their meningiomas in our records. Ten patients (67%) had a potential differential diagnosis mentioned in the radiologist's interpretation, or in clinical notes. The differential diagnoses included metastasis, schwannoma, pituitary macroadenoma, sarcoidosis, choroid plexus papilloma and ependymoma.

In contrast to the possible meningiomas, all non-meningioma intracranial tumors identified were negative on PiB PET/CT (SUVmax≤1.1). Eight of the non-meningioma tumors were of types commonly confused with meningiomas; metastases (2), pituitary macroadenomas (3), schwannomas (2) and an ependymoma. Other non-meningioma tumors included subependymal nodules, lipomas, choroid xanthogranulomas, pineal tumors, Rathke cleft cysts and a glioma. Numerous non-tumorous lesions were seen, including sub-acute to chronic ischemic and hemorrhagic strokes, arachnoid cysts and multiple sclerosis lesions that showed only trace PiB activity. Bony lesions such as hemangiomas, fibrous dysplasia, hyperostosis frontalis and an osteoma had PiB activity similar to, or only slightly higher than normal bone (SUVmax<1.0). Extra-cranial tumors, such as sinus polyps, mucus retention cysts, mucocele, Warthin's tumors and an inverted papilloma also had low PiB activity (SUVmax<1.2). Vascular lesions had blood-pool-level PiB activity or less (SUVmax≤1.2), including aneurysms, telangiectasias, cavernomas and venous angiomas.

PiB PET/CT of Meningiomas Compared to Metastases

Figure 4:
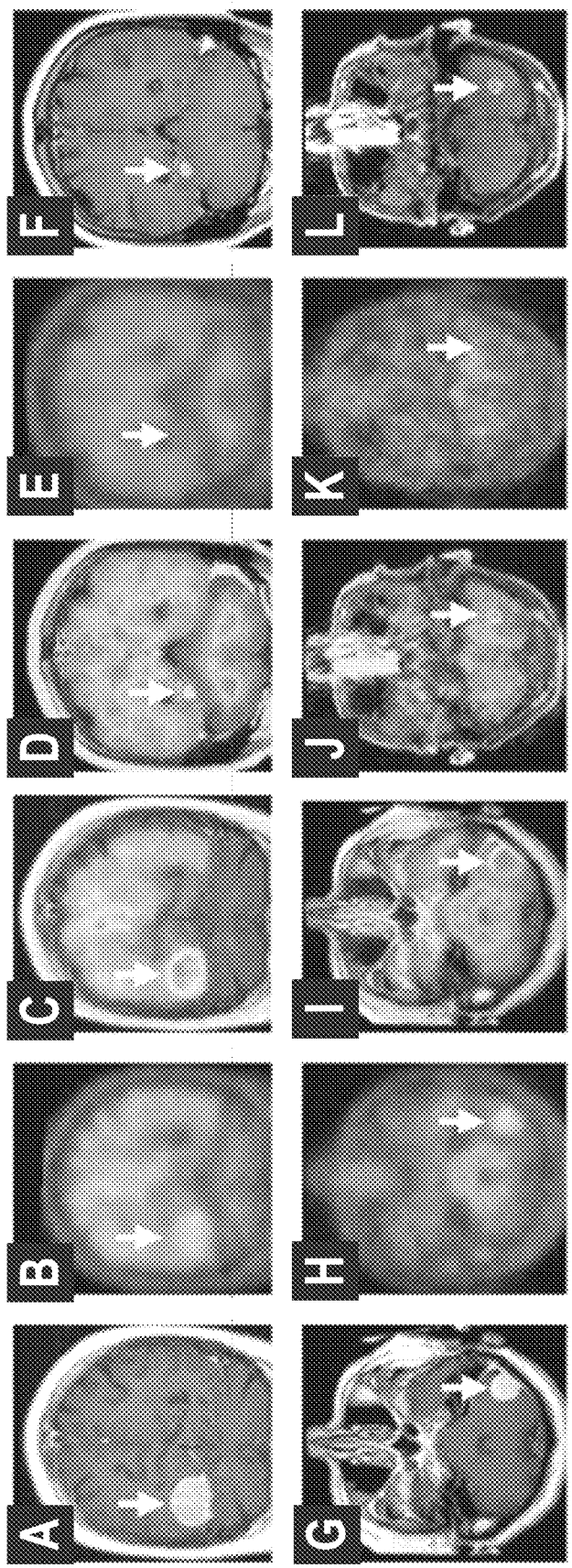
FIG. 4 shows meningiomas compared to metastases on PET using the compound of formula (V) fused to MRI.

Meningiomas and intracranial metastases could be clearly differentiated with PiB PET/CT. FIG. 4 shows two examples. Both metastases were negative on PiB PET/CT. Both metastases were later confirmed pathologically, from autopsy and surgery respectively.

FIG. 4 shows meningiomas compared to metastases on PiB PET fused to MRI. Two high-likelihood meningiomas on the left with contrast enhanced T1-weighted MRI, PiB PET and PiB PET fused to MRI (Panels A-C and G-I) compared to a melanoma metastasis (Panels D-F) and a small cell lung cancer metastasis (Panels J-L) in similar locations. SUVmax of the tumors were 2.8 and 3.6 for the meningiomas and 0.9 and 1.1 for the melanoma and small cell lung cancer metastases respectively. Both metastases and the meningioma in panels G-I had increased FDG PET activity (not shown).

PiB PET/CT of Meningiomas Compared to Other Primary Tumors

Figure 5:
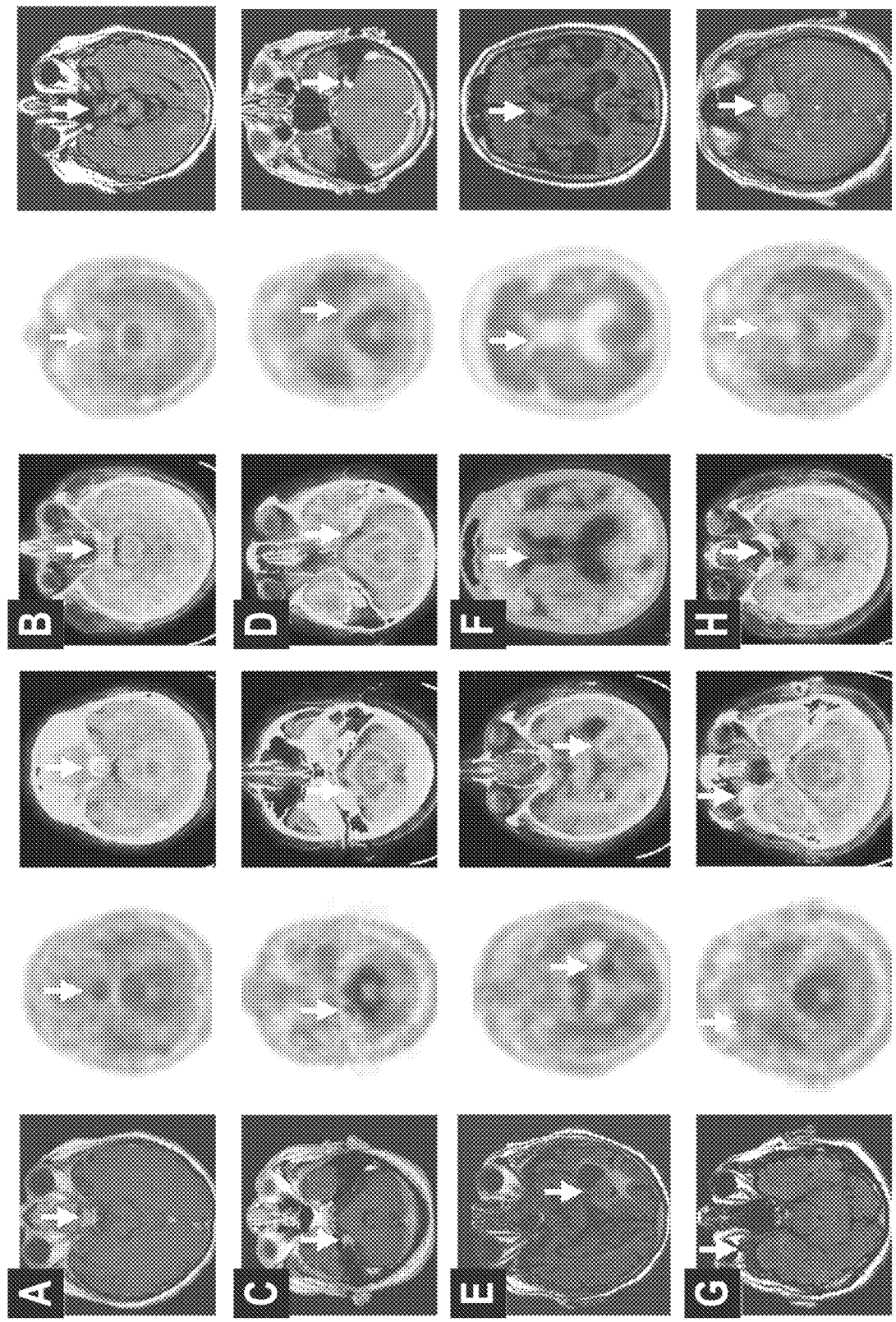
FIG. 5 shows meningiomas compared to other intracranial tumors on PET/CT using the compound of formula (V) and MRI.

Meningiomas and other common primary intracranial tumors could be clearly differentiated with PiB PET/CT. FIG. 5 shows comparison examples of meningiomas and non-meningiomas in similar locations. In all the examples shown the presumed tumor diagnosis was fairly confident with follow-up MRI imaging alone. With the exception of the recurrent meningioma (panel G) and the lateral ventricle meningioma (panel E), none of the tumors shown have been biopsied to date. The meningioma in the lateral ventricle was investigated during a post mortem autopsy, and revealed a WHO grade I meningioma, transitional type in the atrium of the left ventricle measuring 2.2×2.0×1.6 cm. Of note, this type of meningioma has been shown to not contain beta-amyloid by others. We stained multiple meningiomas of this type with anti beta-amyloid antibody and all have been negative. However, all have stained positive with 6-CN-PiB.

FIG. 5 also shows two patients with previously surgically resected meningiomas; one with recurrent meningioma and one with post-surgical scar. Of note, the recurrent meningioma shown in FIG. 5 panels M&N did not meet our criteria for high-probability meningioma, because there was no record of a contrast enhanced MRI performed in this patient. Despite this, the tumor showed slow growth over 40+ years and was very likely a recurrent meningioma.

FIG. 5 shows meningiomas compared to other intracranial tumors on PIB PET/CT and MRI. Sella/supracellar region: Enhanced T1-weighted MRI, PiB PET and PET/CT of a meningioma (SUVmax 1.7, Panel A) compared to PiB PET/CT, PET and FLAIR MRI of a pituitary macroadenoma (SUVmax 0.9, Panel B). The macroadenoma was positive on FDG PET/CT (not shown). Internal auditory canal: Enhanced T1-weighted MRI, PiB PET and PET/CT of a meningioma (SUVmax 1.9, Panel C) compared to PiB PET/CT, PET and enhanced T1-weighted MRI of a schwannoma (SUVmax 0.8, Panel D). Lateral ventricle: FLAIR MRI, PET and PiB PET/CT of a meningioma (SUVmax 2.1, Panel E) compared to PiB PET/CT, PET and FLAIR MRI of an ependymoma (SUVmax 0.4, Panel F). Note the high level of nonspecific PiB activity in nearby normal white matter. Post-surgical meningioma recurrence versus scar FLAIR MRI, PiB PET and PET/CT of meningioma recurrence (SUVmax 1.5, Panel G) compared to PiB PET/CT, PET of postoperative changes/scarring (SUVmax 0.6, Panel H) and enhanced T1-weighted MRI of the pre-surgical tumor (Panel H). Pathology from the initial resections of both tumors showed WHO grade I meningiomas.

Immunohistochemistry for Amyloid

Five surgically resected benign meningiomas all stained negative with amyloid specific antibodies (see example in FIG. 6). Alzheimer diseased brain tissue was used as positive control and stained positively (not shown).

Fluorescent PiB Staining

Fluorescent microscopy of meningiomas stained with PiB revealed a unique staining pattern. To further investigate the mechanism of PiB binding in meningiomas, surgical and autopsy specimens of intracranial tumors were stained with PiB (not shown). PiB, like its parent compound thioflavin-T, has some autofluorescence. These tumor tissues were also stained with a highly fluorescent version of PiB (6-CN-PiB). FIG. 6 shows an example meningioma stained positively with 6-CN-PiB. 6-CN-PiB stained with a similar pattern to PiB, and allowed for better fluorescent images due to higher signal to background ratio.

FIG. 6 shows meningioma tissue stains compared to a schwannoma and amyloid plaques in the cerebral cortex. Enhanced T1-weighted MRI of a meningioma (Panel A) that was later surgically resected and stained with H&E (5x, Panel B), showing a classic appearance for a WHO grade I meningothelial meningioma. Anti-amyloid antibody immunohistochemical staining (antibody clone 6F/3D) of the same meningioma shows complete absence of stain (Panel C), indicating lack of beta-amyloid. 6-CN-PiB staining of the same meningioma shows intense fluorescence (Panel D). This is compared to a schwannoma, which shows only trace fluorescence (Panel E) and amyloid laden cerebral cortex from a patient who had Alzheimer's disease, which shows very intense fluorescence of beta-amyloid plaques (positive control).

The staining in all meningiomas (n=7) was qualitatively brighter than that seen in other intracranial tumors (n=6). The pattern of staining in meningiomas was reproducible with WHO grade 1, 2 and 3 meningiomas. This pattern of staining differed dramatically from that seen in Alzheimer's diseased brain gray matter (FIG. 4), and normal brain white matter (not shown). Normal brain gray matter showed almost no fluorescence (not shown). Moderate 6-CN-PiB binding was seen in some other tumors, but the staining pattern was different. For example, scattered fluorescence in a lung cancer metastasis may have been due to nonspecific binding in areas of tissue necrosis (not shown), and therefore may not directly correlate to findings on PET scans.

Figure 7:
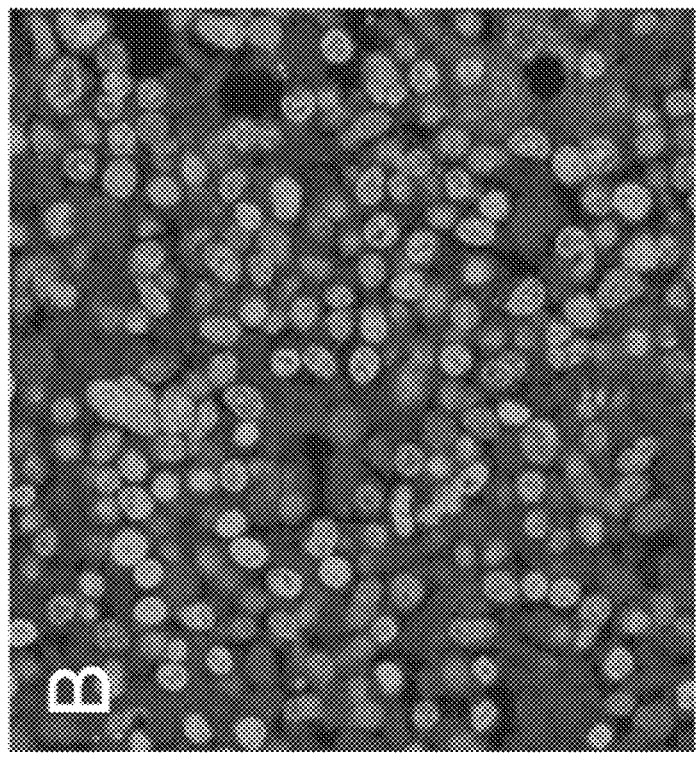
FIG. 7 shows pathologic staining of a small cell lung cancer brain metastasis.
Figure 7:
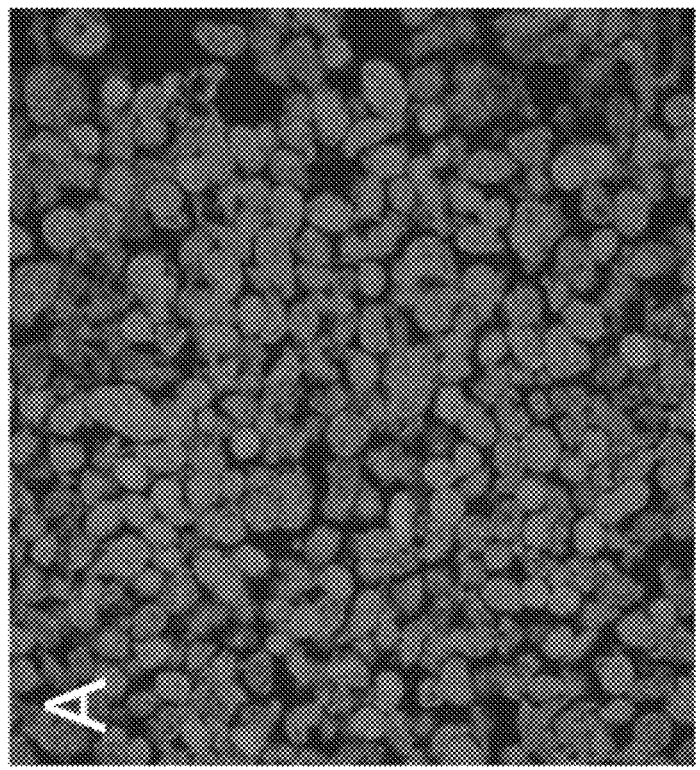

FIG. 7 shows pathologic staining of a small cell lung cancer brain metastasis. The metastasis is the same one shown in PiB PET/CT, PiB PET and MRI imaging in FIG. 4 panels J, K and L, and was obtained at post-mortem autopsy. This metastasis was shown in FIG. 4 to be negative with low activity on PiB PET/CT scan. Surprisingly, this small cell lung cancer metastasis stained with 6-CN-PiB (panel A), showing staining in the nuclei of the cells. This pattern mimics the DNA binding agent POPO-3 used to counter stain the same tumor (panel B). Presumably this pattern of nuclear staining is due to interactions specific to the milieu of the sectioned and prepared tissue and does not reflect conditions in-vivo. Thioflavin-T, of which PiB is a derivative, is known to bind to DNA in a non-specific manner, which may explain this phenomenon. There is no 6-CN-PiB staining outside the nuclei of the metastases. A similar pattern of nuclear staining was seen in the melanoma metastasis shown in FIG. 4 panels D, E and F (not shown). In meningiomas we have seen similar 6-CN-PiB staining in the nuclei (example FIG. 6, panel D), but also see 6-CN-PiB staining outside the nuclei, within the cytoplasm and/or cell membrane. Therefore, we have shown that PiB specifically targets and accumulates in meningiomas in-vivo, which can be seen on PET/CT. PiB is targeting the meningioma outside of the nucleus, likely in the cytoplasm, cell membranes and extracellular matrix of the meningiomas where is binds diffusely, and the target within meningiomas is not beta-amyloid.

DISCUSSION

We have shown here in a study in 834 patients that PiB PET/CT can identify meningiomas and differentiate from other intracranial tumors, including metastases. Our data shows PiB PET/CT to be 100% sensitive and specific for meningiomas 5 mm and thicker compared to all other tumors identified in the population studied. PiB was initially designed to bind to amyloid plaques seen in the brains of patients with Alzheimer disease. However, we provide evidence here that meningiomas do not contain amyloid and that PiB may be binding to something novel and perhaps unique to meningiomas. Tissue stains suggest the most likely binding location is within the nuclei of the cells of the meningiomas, and may reside within areas of heterochromatin.

PiB PET/CT may help resolve common diagnostic dilemmas in brain tumor diagnosis. While many meningiomas are diagnosed with confidence on follow-up MRI scans, differentiating meningiomas from life-threatening brain tumors on a single scan presents a challenge. The general categories or etiologies of meningioma-like masses include metastatic disease, lymphoma, plasmacytoma, primary dural tumors, infections, inflammatory tumors, and other systemic diseases. Metastases are the most common tumors to be confused with meningiomas and often require drastically different therapy. In addition to meningeal spread, metastases are seen commonly in the peripheral brain parenchyma, where they can be indistinguishable from meningeal masses on MRI and CT.

The clinical scenario of the patient in our study with melanoma metastasis emphasizes the potential usefulness of this technology. In this case the tumor was incidentally detected on an MRI that was performed for evaluation of a stroke. This patient had her primary melanoma resected from her neck six years prior. She had no history of metastasis. Whole body FDG PET/CT did not reveal any other tumors. The radiologist's interpretation of the initial brain MRI gave a differential that included meningioma and metastasis; therefore follow-up MRI scans were performed. On follow-up imaging over five months rapid tumor growth was seen, which lead to brain biopsy for final diagnosis. Pathology showed the metastasis was actually in the periphery of the cerebral cortex, not truly in the meninges. At initial imaging the tumor was large enough to be detectable by PET/CT technology, as it was positive on FDG PET/CT. But since meningiomas can be FDG avid, this did not narrow the differential diagnosis. However, the tumor was negative on the research PiB PET/CT. Therefore, based on the data we present in this study, the tumor was unlikely to be a meningioma, and aggressive therapy could have been initiated much earlier.

CONCLUSIONS

We show here that PiB PET/CT has the potential to become a useful adjunct to MRI and CT imaging for the diagnosis of meningiomas. Tumor imaging with PiB PET/CT represents a new type of tumor imaging not previously described. The exact mechanism of PiB binding in meningiomas is not clear, but PiB is likely binding to something other than amyloid within meningiomas.

From our studies, we conclude that: (1) PiB targets meningiomas in-vivo; (2) PiB PET/CT identifies meningiomas; (3) PiB PET/CT is highly sensitive for meningiomas; (4) PiB PET/CT does not identify other tumors, including metastases; (5) PiB PET/CT is specific for meningiomas; (6) CN-PiB nuclear staining is likely unrelated to PiB binding in-vivo (artifact of tissue staining conditions)—CN-PiB nuclear staining is seen in PiB PET/CT negative metastases; (7) Meningiomas do not contain beta-amyloid; (8) PiB is not binding beta-amyloid in meningiomas; and (9) PiB is targeting meningioma cell cytoplasm, membrane or extracellular matrix (non-nuclear). Thus, PiB is binding specifically to non-beta-amyloid, non-nuclear parts of the meningiomas.

Prophetic Example A

One would administer the compound of Formula (X) to a patient with presumed meningioma. The compound of formula (X) is also known as Florbetapir, or $^{18}$F-AV-45. One would acquire a combined PET/CT image to detect the presence or absence of any meningiomas in the patient. One would envision that PET/CT data would confirm meningioma uptake of Formula (X). One would envision that other stilbene derivatives would confirm meningioma uptake.

Prophetic Example B

One would administer the compound of Formula (XI) to a patient with presumed meningioma. The compound of formula (XI) is also known as Florbetapen, or AV-1, or BAY94-9172. One would acquire a combined PET/CT image to detect the presence or absence of any meningiomas in the patient. One would envision that PET/CT data would confirm meningioma uptake of Formula (XI). One would envision that other stilbene derivatives would confirm meningioma uptake.

Prophetic Example C

One would administer the compound of Formula (XII) to a patient with presumed meningioma. The compound of formula (XIV) is also known as AV-144. One would acquire a combined PET/CT image to detect the presence or absence of any meningiomas in the patient. One would envision that PET/CT data would confirm meningioma uptake of Formula (XII). One would envision that other biphenylalkyne derivatives would confirm meningioma uptake.

Prophetic Example D

One would administer the compound of Formula (XIII) to a patient with presumed meningioma. The compound of formula (XIII) is also known as AV-138. One would acquire a combined PET/CT image to detect the presence or absence of any meningiomas in the patient. One would envision that PET/CT data would confirm meningioma uptake of Formula (XIII). One would envision that other biphenylalkyne derivatives would confirm meningioma uptake.

Prophetic Example E

One would administer the compound of Formula (XIV) to a patient with presumed meningioma. The compound of formula (XIV) is also known as AV-19. One would acquire a combined PET/CT image to detect the presence or absence of any meningiomas in the patient. One would envision that PET/CT data would confirm meningioma uptake of Formula (XIV). One would envision that other stilbene derivatives would confirm meningioma uptake.

Prophetic Example F

One would administer the compound of Formula (XVII) to a patient with presumed meningioma. The compound of formula (XVII) is also known as $^{125}$I-IMPY. One would acquire a combined PET/CT image to detect the presence or absence of any meningiomas in the patient. One would envision that PET/CT data would confirm meningioma uptake of Formula (XVII). One would envision that other imidazo[1,2-a]pyridine derivatives would confirm meningioma uptake.

Prophetic Example G

Method of Treating Meningiomas

In one embodiment, the present invention provides a method for treating a meningioma in a subject. The method includes the step of administering to the subject a therapeutically effective amount of a composition including a cytotoxic agent associated with a phenylbenzothiazole derivative or a stilbene derivative or a biphenylalkyne derivative or an imidazo[1,2-a]pyridine derivative that accumulates within meningiomas. In a preferred embodiment, one can obtain a diagnosis of meningioma in a subject as illustrated in Examples 1-4 and Prophetic Examples A-F above. Once identified as a subject, a therapeutically effective amount of a composition including a cytotoxic agent associated with a phenylbenzothiazole derivative or a stilbene derivative or a biphenylalkyne derivative or an imidazo[1,2-a]pyridine derivative that accumulates within meningiomas (such as Formulas (I) to (XVII) above) will be administered to the subject. The subject would then be imaged using one or more of the medical imaging techniques described herein to assess whether the reduction of meningioma symptoms has occurred. Dosing regimens can be derived from brain cancer treatment. Preferably, tumor measurements for response will be checked every month. One would envision that a composition according to the invention including a cytotoxic agent associated with a phenylbenzothiazole derivative or a stilbene derivative or a biphenylalkyne derivative or an imidazo[1,2-a]pyridine derivative would treat the meningioma.

Thus, the invention provides a method for the treatment of meningiomas using a therapeutically effective amount of a composition including a cytotoxic agent associated with a phenylbenzothiazole derivative or a stilbene derivative or a biphenylalkyne derivative or an imidazo[1,2-a]pyridine derivative that accumulates within meningiomas. More particularly, the invention provides a method for the treatment of meningiomas using a composition including a cytotoxic agent associated with Pittsburgh compound B.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for treating a meningioma in a subject, the method comprising:
   (a) administering to the subject, in need thereof, a therapeutically effective amount of a composition including a cytotoxic agent associated with a compound of

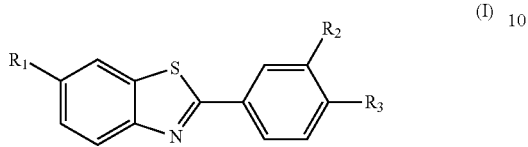

formula (I):
   wherein the compound is targeted to any meningiomas in the subject,
   wherein $R_1$ is selected from the group consisting of H, OH, halogen, substituted or unsubstituted alkyl, substituted or unsubstituted alkoxy, substituted or unsubstituted amino, and substituted or unsubstituted carboxylate,
   wherein $R_2$ is selected from the group consisting of H, OH, halogen, substituted or unsubstituted alkyl, substituted or unsubstituted alkoxy, substituted or unsubstituted amino, and substituted or unsubstituted carboxylate,
   wherein $R_3$ is selected from the group consisting of H, OH, halogen, substituted or unsubstituted alkyl, substituted or unsubstituted alkoxy, substituted or unsubstituted amino, and substituted or unsubstituted carboxylate,
   wherein the composition does not interact with amyloid-beta within meningiomas in the treated subject, and
   wherein the meningiomas in the subject do not contain amyloid-beta.

2. The method of claim 1 wherein:
   $R_1$ is OH.

3. The method of claim 1 wherein:
   $R_2$ is H.

4. The method of claim 1 wherein:
   $R_3$ is $NH^{11}CH_3$.

5. The method of claim 1 wherein:
   $R_1$ is OH,
   $R_2$ is H, and
   $R_3$ is $NH^{11}CH_3$.

6. The method of claim 1 wherein:
   $R_1$ is OH,
   $R_2$ is F, and
   $R_3$ is $NH^{11}CH_3$.

7. The method of claim 1 further comprising before step (a):
   (i) administering to the subject a detectable amount of the compound of formula (I) wherein at least one of the atoms in $R_1$ or $R_2$ or $R_3$ is replaced with $^3H$, $^{11}C$, $^{13}C$, $^{14}C$, $^{13}N$, $^{15}O$, $^{75}Br$, $^{76}Br$, $^{18}F$, $^{19}F$, $^{68}Ga$, $^{82}Rb$, $^{111}In$, $^{123}I$, $^{125}I$, $^{131}I$, $^{201}Tl$, and $^{99m}Tc$;
   (ii) acquiring an image to detect the presence or absence of any meningiomas in the subject; and
   (iii) if the presence of any meningiomas is detected in the subject, then performing step (a).

8. The method of claim 7 wherein:
   step (ii) comprises acquiring the image using an imaging method selected from positron emission tomography imaging, single photon emission computed tomography imaging, positron emission tomography with computed tomography imaging, positron emission tomography with magnetic resonance imaging, single photon emission computed tomography with computed tomography imaging, or any combination thereof.

9. The method of claim 7 wherein:
   step (ii) comprises acquiring the image using positron emission tomography imaging.

10. The method of claim 7 wherein:
    step (ii) comprises acquiring the image using single photon emission computed tomography imaging.

11. The method of claim 7 wherein:
    step (ii) comprises acquiring the image using positron emission tomography with computed tomography imaging.

12. The method of claim 7 wherein:
    step (ii) comprises acquiring the image using positron emission tomography with magnetic resonance imaging.

13. The method of claim 7 wherein:
    step (ii) comprises acquiring the image using single photon emission computed tomography with computed tomography imaging.

14. The method of claim 7 wherein:
    the presence of any meningiomas in the subject is indicated by an image in which meningiomas showed activity of the compound greater than normal adjacent tissues imaged.

15. The method of claim 7 wherein:
    the presence of any meningiomas in the subject is indicated by a brain image in which meningiomas showed activity of the compound greater than any other intracranial tumors imaged.

16. The method of claim 7 wherein:
    the presence of any meningiomas in the subject is indicated by a brain image in which meningiomas showed activity of the compound greater than any metastases, pituitary macroadenomas, schwannomas, or ependymomas imaged.

17. The method of claim 7 wherein:
    the presence of any meningiomas in the subject is indicated by an image in which meningiomas showed activity of the compound greater than any metastases imaged.

18. The method of claim 1 wherein:
    the cytotoxic agent is selected from cytotoxins, chemotherapeutic agents, radiation-emitters, and combinations thereof.

19. The method of claim 1 wherein:
    the cytotoxic agent is a radiation-emitter.

20. The method of claim 19 wherein:
    the radiation-emitter is a radioisotope.

21. The method of claim 19 wherein:
    the radiation-emitter is selected from the group consisting of phosphorus-32, phosphorus-33, bromine-77, yttrium-88, yttrium-90, molybdenum-99m, technetium-99m, indium-111, indium-131, iodine-123, iodine-124, iodine-125, iodine-131, lutetium-177, rhenium-186, rhenium-188, bismuth-212, bismuth-213, astatine-211, and combinations thereof.

22. The method claim 1 wherein:
the cytotoxic agent is a cytotoxin selected from the group consisting of ricin, pseudomonas exotoxin, diphtheria toxin, and combinations thereof.

23. The method of claim 1 wherein:
the composition is administered parenterally.

24. The method of claim 1 wherein:
the composition does not cross the blood brain barrier of the subject.

25. The method of claim 1 wherein:
the cytotoxic agent is a chemotherapeutic agent selected from the group consisting of alkylating agents, antagonists, plant alkaloids, intercalating antibiotics, enzyme inhibitors, antimetabolites, mitotic inhibitors, growth factor inhibitors, cell cycle inhibitors, enzymes, biological response modifiers, and combinations thereof.

26. A method for treating a meningioma in a subject, the method comprising:
(a) administering to the subject, in need thereof, a therapeutically effective amount of a composition including a cytotoxic agent associated with a compound of formula (V):

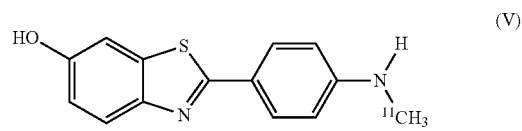

wherein the compound is targeted to any meningiomas in the subject,
wherein the composition does not interact with amyloid-beta within meningiomas in the treated subject, and
wherein the meningiomas in the subject do not contain amyloid-beta.

27. The method of claim 26 further comprising before step (a):
(i) administering to the subject a detectable amount of the compound of formula (V);
(ii) acquiring an image to detect the presence or absence of any meningiomas in the subject; and
(iii) if the presence of any meningiomas is detected in the subject, then performing step (a).

* * * * *

UNITED STATES PATENT AND TRADEMARK OFFICE
CERTIFICATE OF CORRECTION

PATENT NO. : 10,940,218 B2  
APPLICATION NO. : 15/472763  
DATED : March 9, 2021  
INVENTOR(S) : Geoffrey B. Johnson et al.

Page 1 of 1

It is certified that error appears in the above-identified patent and that said Letters Patent is hereby corrected as shown below:

In the Specification

Column 12, Line 53, "$^{11}C, ^{13}, ^{14}C$" should be -- $^{11}C, ^{13}C, ^{14}C$ --.

Signed and Sealed this  
Twenty-seventh Day of April, 2021

Drew Hirshfeld  
*Performing the Functions and Duties of the*  
*Under Secretary of Commerce for Intellectual Property and*  
*Director of the United States Patent and Trademark Office*